United States Patent [19]

Schilling, Jr. et al.

[11] Patent Number: 4,933,280

[45] Date of Patent: Jun. 12, 1990

[54] RECOMBINANT DNA SEQUENCE ENCODING ALVEOLAR SURFACTANT PROTEIN

[75] Inventors: James W. Schilling, Jr., Palo Alto; Robert T. White, Fremont; Barbara Cordell; Bradley J. Benson, both of San Francisco, all of Calif.

[73] Assignee: California Biotechnology Inc., Mountain View, Calif.

[21] Appl. No.: 857,715

[22] Filed: Apr. 30, 1986

Related U.S. Application Data

[63] Continuation-in-part of Ser. No. 808,843, Dec. 13, 1985, which is a continuation-in-part of Ser. No. 480,358, Dec. 11, 1984, Pat. No. 4,659,805.

[30] Foreign Application Priority Data

| Dec. 10, 1985 | [WO] | PCT Int'l Appl. .................. PCT/US85/02445 |
| Dec. 11, 1985 | [IR] | Iran ........................................ 3133/85 |
| Dec. 11, 1985 | [IL] | Israel ........................................ 77296 |
| Dec. 11, 1985 | [ES] | Spain ........................................ 549817 |

[51] Int. Cl.$^5$ .................. C12P 21/02; C12N 15/00; C12N 1/00; C07K 13/00
[52] U.S. Cl. .................. 435/69.1; 435/172.3; 435/320; 935/11; 530/350
[58] Field of Search .................. 435/172.3, 68, 240, 435/317; 935/11

[56] References Cited

U.S. PATENT DOCUMENTS

4,312,860 1/1982 Clements .
4,562,003 12/1985 Lewicki ................................ 435/68

OTHER PUBLICATIONS

Sueishi et al, Biochimica et Biophysica Acta, vol. 665, pp. 442-453.
Katzal et al, Biochimica et Biophysica Acta, vol. 670, pp. 323-331 (1981).
Hewick et al, Journal of Biol. Chem., vol. 256, pp. 7990-7997 (1981).
Hunkapiller et al, Methods In Enzymology, vol. 91, pp. 399-413 (1983).
Chirgwin et al, Biochemistry, vol. 18, pp. 5294-5299 (1979).
Breslow et al, PNAS USA, vol. 79, pp. 6861-6865, Nov. 1982.
Young et al, PNAS USA, vol. 80, pp. 1194-1198, Mar. 1983.
Helfman et al, PNAS USA, vol. 80, pp. 31-35, Jan. 1983.
Brandwein et al, PNAS USA, vol. 78, pp. 4241-4245, Jul. 1981.
King, R. J., et al, *Am J. Physiol* (1973) 224:788-795.
Hallman, M., et al, *Pediatric Clinics in North America* (1982) 29:1057-1075.
Fujwara, et al, *Lancet* (1980) 1:55.
Hallman, M., et al, *Pediatrics* (1983) 71:473-482.

*Primary Examiner*—Alvin E. Tanenholtz
*Attorney, Agent, or Firm*—Irell & Manella

[57] ABSTRACT

The complete coding sequences and amino acid sequences for both canine and human 32K alveolar surfactant proteins (ASP) are disclosed; clones for the 10K protein have also been obtained. Methods and vectors for obtaining these proteins in recombinant form are described. The availability of large amounts of these proteins through recombinant techniques permits the use of ASP in suitable pharmaceutical compositions in the treatment of respiratory deficiency syndromes.

14 Claims, 30 Drawing Sheets

```
                                            -17
TCT  GGA  GAG  TCA  CTG  GAC  GAA  GCC  ATG
Ser  Gly  Glu  Ser  Leu  Asp  Glu  Ala  MET

TGG  CTG  CGC  TGT  TTG  GCC  CTC  GCC  CTC
Trp  Leu  Arg  Cys  Leu  Ala  Leu  Ala  Leu
                         ←signal sequence | mature ASP sequence→
                                  -1    1
ACC  TTG  CTG  ATG  GTT  TCT  GGC  ATC  GAG
Thr  Leu  Leu  MET  Val  Ser  Gly  Ile  Glu

*  #375                #374        10
AAC  AAT  ACG  AAG  GAC  GTC  TGT  GTT  GGA
Asn  Asn  Thr  Lys  Asp  Val  Cys  Val  Gly

20
AAC  CCT  GGC  ATC  CCT  GGC  ACT  CCT  GGG
Asn  Pro  Gly  Ile  Pro  Gly  Thr  Pro  Gly

TCC  CAT  GGC  TTG  CCA  GGC  AGA  GAT  GGG
Ser  His  Gly  Leu  Pro  Gly  Arg  Asp  Gly

30
AGA  GAT  GGA  GTC  AAA  GGA  GAC  CCT  GGG
Arg  Asp  Gly  Val  Lys  Gly  Asp  Pro  Gly

40
CCT  CCA  GGC  CCA  TTG  GGC  CCC  CCT  GGA
Pro  Pro  Gly  Pro  Leu  Gly  Pro  Pro  Gly

50
GGA  ATG  CCA  GGC  CAC  CCT  GGG  CCT  AAT
Gly  MET  Pro  Gly  His  Pro  Gly  Pro  Asn
```

FIG. 1-1

```
                    60
GGG ATG ACT GGA GCC CCT GGT GTT GCT
Gly MET Thr Gly Ala Pro Gly Val Ala

70
GGA GAG CGT GGA GAA AAG GGA GAG CCT
Gly Glu Arg Gly Glu Lys Gly Glu Pro

80
GGC GAG AGG GGC CCC CCA GGA CTT CCA
Gly Glu Arg Gly Pro Pro Gly Leu Pro

90
GCT TCT TTA GAT GAA GAG CTC CAA ACC
Ala Ser Leu Asp Glu Glu Leu Gln Thr

100
ACA CTC CAC GAC CTC AGA CAT CAA ATC
Thr Leu His Asp Leu Arg His Gln Ile

110
CTG CAG ACC ATG GGA GTC CTC AGC TTG
Leu Gln Thr MET Gly Val Leu Ser Leu

CAC GAG TCC CTG CTG GTG GTG GGA AGG
His Glu Ser Leu Leu Val Val Gly Arg

120
AAG GTC TTC TCC AGC AAT GGG CAG TCC
Lys Val Phe Ser Ser Asn Gly Gln Ser

130
ATT AAT TTC AAC GAC ATT CAA GAG TTA
Ile Asn Phe Asn Asp Ile Gln Glu Leu
```

FIG. 1-2

```
              140
TGT GCC GGG GCA GGC GGC CAA ATT GCT
Cys Ala Gly Ala Gly Gly Gln Ile Ala

150
GCC CCG ATG AGC CCA GAA GAG AAT GAA
Ala Pro MET Ser Pro Glu Glu Asn Glu

160
GCC GTT GCA AGC ATT GTG AAG AAG TAT
Ala Val Ala Ser Ile Val Lys Lys Tyr

170
AAC ACT TAC GCC TAC CTG GGC CTG GTG
Asn Thr Tyr Ala Tyr Leu Gly Leu Val

180
GAG AGC CCC GAC TCT GGA GAC TTC CAG
Glu Ser Pro Asp Ser Gly Asp Phe Gln

*
TAC ATG GAT GGG GCC CCT GTG AAT TAC
Tyr MET Asp Gly Ala Pro Val Asn Tyr

200
ACC AAC TGG TAC CCC GGG GAG CCC AGA
Thr Asn Trp Tyr Pro Gly Glu Pro Arg

GGT CGG GGC AAA GAG CAG TGT GTG GAG
Gly Arg Gly Lys Glu Gln Cys Val Glu

210
ATG TAC ACA GAT GGG CAG TGG AAT AAC
MET Tyr Thr Asp Gly Gln Trp Asn Asn
```

FIG. 1-3

```
            220
AAA AAC TGC CTG CAG TAC CGA CTG GCC
Lys Asn Cys Leu Gln Tyr Arg Leu Ala

230
ATC TGT GAG TTT TGA gca gcc tct aag
Ile Cys Glu Phe End gcc aca gta gag ata ggc cct gcc ttg ctt tca gcc tcc atc ctg cag
```

```
                                                                                                  900
AGTGAATGGTCACCCCAAGAGTCCAAGTGCCAGCTCTGCATGTTTGTAACCACCCAGGCAGGGAACCACAGTGAGCAGGCCACACCACAG
SerGluTrpSerProGlnSerLysCysGlnLeuCysMETPheValThrThrGlnAlaGlyAsnHisSerGluGlnAlaThrProGln
                                            950
GCAATACGGCCAGGCTGCCTCAGCTCCTGGCTGGACAGACAAGTGCGAGCAGTTTGTGAGCAGCACATGCCTGCTGCAGACCCTA
                                                                     1050
AlaIleArgGlnAlaCysLeuSerSerTrpLeuAspArgGlnLysCysGluGlnPheValGlnHisMETProArgLeuGlnThrLeu
GCATCCGGGGCAGGATGCCACACCACCTGCCAGGCCCTGGGGGTGTAGGACCACGTTCAGTCCTCTCCAGTGTATCCATTCCTCAC
AlaSerGlyGlyArgAspAlaThrProProAlaArgProTrpGlyCysArgThrThrPheSerProLeuGlnCysIleHisIleProHis
                                 1100                                   1150
TTCTGACAAGGACTCAAAGCCATGCCAGCCCAAACGAGCCACTTCCTTGTGAGGTGCAGCCAAGGCAGCACCCCTCTGGAGGAGATCCG
Phe                   1200                                                      1250
CAAGAGGGGACTTCCGGCCTTGATAACTTCCGGCCAGAACTCACACCCAGACTGGAGCCAGGCCAGCTCCCGTAACCCCCAGCGCTGGGTC
                                          1300                                  1350
CAGGGAACACATCAGCCACATGCCCTTCCCGCTTGATTCCCTTTCATCTCCATGTCATAAGACTAGCTTTACAGTTATTTGC
                                   1400
TAATACTTTCATAAAACTAAATTCAGGAGAATAAAAATGGACCATGAAGTAGCCTAGAAGATAGATACTGAGAGCAAGCTTTCT
1453
TAAAAATAGGAAT
```

FIG. 2-2

```
                                                                          50
GGA TCC TCC AGC CTG AGT GCT CTT GGG GAA ACA TGC TGT GTA AAC ACT ATG CCC

100
ATT TCC TGC CTG GAG CAC AGG TTT TGT GGT AGG CTC TCA GGG GTG AGG AGA GAA

150           ▼
GCC TGG CAG CCC CCA CAT CTA TAA ATG CTG CGT CTA CCT TAC CCT CTG ACT TGG

▼                       200
AGG CAG AGA CCC AAG CAG CTG GAG GCT CTG TGT GTG GGT GAG TTT AGC CCC ATC

250
CCC TAG GTG TTC TCC AGC TTG AGG ATC GCA GGC AGA GAG GAC CAG CCC AGC AGC

300
CAC AGG CCT GAC CAA AGC CCA GGC TGG AAG GAG GGC AAC TCC CCA TTT CAC

350
TGG GAG GTG TTT CAC AGC ACA GTC AAC ATA GGT GAC CTG CAA AGA TCC TCA TGT

400
TTG TTA TTT TCT TTG GCC AGA TCC ATC CTA CAG GGT TCA GCA GGG CCT ACA GGA

450
GGG GCA GTG AGA GAA CAG ACC CCA AAA AGA AAG GGG ACT CCA TGA CTG ACC ACC

500
TTG AGG GGG GCC AGG CTG CCG GGC CCC GTT CAT CTT TTT TCA TTC TCA GGT CGC

550
TGA TTT CTT GGA GCC TGA AAA GAA AGT AAC ACA GCA GGG ATG AGG ACA GAT GGT

600
GTG AGT CAG TGA GTG AGT GAC CTG ACT AAT AGC CTG GGA GGG ACA GGG CAG GTT 650                                                                   700
TTC TGC AGA GGC ACG GAA GAT TCA GCT GAA GTC AGA GAG GTG AAG CCA GTT TCC
```

FIG. 3-1

```
                                                    750
CAG GGT AAC ATA GTG AGG CAC TGA AAG AAA GGA GAC TGC ACT GGA GCC CAG GTC

800
CCC GGG CTC CCC AGA GCT CCT TAC TCT TCC TCC TCC TCA GCA GCC TGG AGA CCC

850
CAC AAC CTC CAG CCG GAG GCC TGA AGC ATG AGG CCA TGC CAG GTG CCA GGT GAT

900
GCT GGG AAT TTT CCC GGG AGC TTC GGG TCT TCC CAG CAC TCT GGT CGT CGC CCG

950
CCC TGC CTC GTC GGG CTC TGC CCA GCT TCC TGA GTC CTG ACA GAG CAC AGT GGG

1000
GAG ATG TTG GCA GAG GTG GCA GAT GGG CTC ACG GCC ATC CCT CCT GCA GGA GCA
    MET Leu Ala Glu Val Ala Asp Gly Leu Thr Ala Ile Pro Pro Ala Gly Ala

1050
GCG ACT GGA CCC AGA GCC ATG TGG CTG TGC CCT CTG GCC CTC AAC CTC ATC TTG
Ala Thr Gly Pro Arg Ala MET Trp Leu Cys Pro Leu Ala Leu Asn Leu Ile Leu

1100          ▼
ATG GCA GCC TCT GGT GCT GTG TGC GAA GTG AAG GAC GTT TGT GTT|GGA AGC CCT
MET Ala Ala Ser Gly Ala Val Cys Glu Val Lys Asp Val Cys Val|Gly Ser Pro
              ◀—signal sequence—| |—mature ASP sequence—▶
         1150        BamHI                              *
GGT ATC CCC GGC ACT CCT GGA TCC CAC GGC CTG CCA GGC AGG CAC GGG AGA GAT
Gly Ile Pro Gly Thr Pro Gly Ser His Gly Leu Pro Gly Arg His Gly Arg Asp

*    1200    **
GGT CTC AAA GGA GAC CTG GGC CCT CCA G GTAC TGT GCT GCA GAC CCC ACC CTC
Gly Leu Lys Gly Asp Leu Gly Pro Pro G

1250
AGC TGA GGA CAC AGA CCC CTT TTC AGG AGG CCC ATC TGT CCA GGC CCC TAG GCT 1300                                                              1350
GTG GGC CAT AGT GAG CTG GGG GCT ATA GTA AGC TGG GTG GGA CTT CAG TCT GCA
```

FIG. 3-2

```
                                                              1400
GGG CTG GTG GGT TCC TGG GGC CCT TAT GAT GGC GCA TCC TGG AGA GTC TGT CCT

1450
CAT AGT GCC CAC GGA GTG ATA GAG TGA TAG CTG AGC CAG CCC TGG TGA TAA TGG

1500
GCA TCG AGT CTC ACT AGC TCC AAC CAG TTG TGG GTG ACA GAT CCT ACA CAT CCA

ExonII               1550
TGT CTC TTT TCT CTG CAG GC CCC ATG GGT CCA CCT GGA GAA ATG CCA TGT CCT
                            ly Pro MET Gly Pro Pro Gly Glu MET Pro Cys Pro 1600
CCT GGA AAT GAT GGG CTG CCT GGA GCC CCT GGT ATC CCT GGA GAG TGT GGA GAG
Pro Gly Asn Asp Gly Leu Pro Gly Ala Pro Gly Ile Pro Gly Glu Cys Gly.Glu 1650
AAG GGG GAG CCT GGC GAG AGG GGC CCT CCA G GTG AGC AGG GTG GGG CAG GTG GGC
Lys Gly Glu Pro Gly Glu Arg Gly Pro Pro G

1700
AGT GGA AAC ATG GGC ACA GCG ACC CTG AAG TCA GTT ACA CGG GGA TGA TGG GGA

1750
TCA GAC AAA CCC TAC AGG TTC CCC AAG GGC ATT TGG CTC AAC CTA AGT AAG AGA

HindIII      1800
GGA TAA GCT TGA GGG AGA AAG CTG AGG TGT CTG GGG AGT GTG GTC ACA ATT CAG

1850
GGA AAG GCA GGT GTG GGA AGT CCT CCG TGC CTC ATG ACC ACC GAT GGG GAC ACA

1900
CTG AGT CAG GTG TGG GAT GAG GGA CAG CAC TGG GAG GCA GGG GAG GCA TGT CCT

1950
GGG ATG GAG GCC CTG GGG CTG TCT GAA GGG TGA ATG CGG ACG AGG CAT CCA GAC
```

FIG. 3-3

```
2000                                                       2050
AGA CGG TGT GAT CAG GAG CCC CAC AGA CAG AGG GGA ACT TTG AAG CTC AGA GCG

2100
GTA AGC AAG TCC ATC AGG GCA GTG CAG AGA GCA TCA TGC TTG CCC TTC GGT CGG

2150
AGG GTG CGG GAG AGG GAC TTG CCC CAC AGA GGC GGG CAG ACA GAA CCC CTC GAG

2200
GAC AAG AGC AGG AAA GAG GAC AAG GGG TGG GGG TCT CAG CAG GGG CAA GGC TTC

2250
ACT AAA GAA TAG GGG ACC ACG GGT CTG AGA CAC ACT GGA ATC TTG TGG ACC CTC

2300
TGA GCC TAG GTC TGG TGG CGC CTA ACA GCA ATG AAA GGG CAG AGT TCC AGG ATT

2350
GCA GAT GGC AAA ACA CCT CGT GGC AGC AAG TGG GAG TCT TCA CTG GCC TGC CCC

2400        ExonIII
TCC TTC TGT GTG GGG CAC TCT CCA CAG GG CTT CCA GCT CAT CTA GAT GAG GAG
                                        ly Leu Pro Ala His Leu Asp Glu Glu 2450
CTC CAA GCC ACA CTC CAC GAC TTT AGA CAT CAA ATC CTG CAG ACA AGG GGA G GTA
Leu Gln Ala Thr Leu His Asp Phe Arg His Gln Ile Leu Gln Thr Arg Gly A

2500
AGG GGA CCC CCT GGG CTC ACG GGT AGG AG TTT CCC ACA AAT TCC CCT CAT TCT

2550
CAG CAC CAG CTT CTA GAA CAT AGA GAT TAC AAA TAG GCA TGC ACA TGC AGG TCT

2600
TGG GGA AAG GAA TTG ACG CTT GCT TTT CTT GAT GTC TTT TGA ATG GCC CAG AGG
```

FIG. 3-4

```
                                                                      2700
2650
AGA CAG AAG CAG ACA CAA TTC ACT TCC CCG ATT TCA TAG GAA AGC AAG TTC TCT

EcoRI                              2750
ATC TGC CTT GCT TTC CAC TGA ATT CAC AGG AAA TTG CAC CAT TTC TGG CAA TAA

2800
GTA ATT GTT ACT TAG GTG AAT GAA TAA ATG GAG GAG AGT CTA AAA GTG AAT TTA

2850
GAA AAC TGC AAT TGG AAG AGG AAG AGA AGA CAC AGA GAG AGG CAG AGA TGG AGA

2900
GAC TGG GGA GAA TCT GGT AGC AGA GAC CCC AGG TGA GGG AGG TGG CTT AGA GAC

2950           Exon IV
AAA GTG GTC AGT GGC CTG ACC CGG ACT CCT CTG CTC TCAG CC CTC AGT CTG CAG
                                                    la Leu Ser Leu Gln 3000
GGC TCC ATA ATG ACA GTA GGA GAG AAG GTC TTC TCC AGC AAT GGG CAG TCC ATC
Gly Ser Ile MET Thr Val Gly Glu Lys Val Phe Ser Ser Asn Gly Gln Ser Ile 3050
ACT TTT GAT GCC ATT CAG GAG GCA TGT GCC AGA GCA GGC GGC CGC ATT GCT GTC
Thr Phe Asp Ala Ile Gln Glu Ala Cys Ala Arg Ala Gly Gly Arg Ile Ala Val 3100                     HindIII
CCA AGG AAT CCA GAG GAA AAT GAG GCC ATT GCA AGC TTC GTG AAG AAG TAC AAC
Pro Arg Asn Pro Glu Glu Asn Glu Ala Ile Ala Ser Phe Val Lys Lys Tyr Asn 3150
ACA TAT GCC TAT GTA GGC CTG ACT GAG GGT CCC AGC CCT GGA GAC TTC CGC TAC
Thr Tyr Ala Tyr Val Gly Leu Thr Glu Gly Pro Ser Pro Gly Asp Phe Arg Tyr 3200
TCA GAC GGG ACC CCT GTA AAC TAC ACC AAC TGG TAC CGA GGG GAG CCC GCA GGT
Ser Asp Gly Thr Pro Val Asn Tyr Thr Asn Trp Tyr Arg Gly Glu Pro Ala Gly
```

FIG. 3-5

```
                3250
CGG GGA AAA GAG CAG TGT GTG GAG ATG TAC ACA GAT GGG CAG TGG AAT GAC AGG
Arg Gly Lys Glu Gln Cys Val Glu MET Tyr Thr Asp Gly Gln Trp Asn Asp Arg

3300
AAC TGC CTG TAC TCC CGA CTG ACC ATC TGT GAG TTC TGA GAG GCA TTT AGG CCA
Asn Cys Leu Tyr Ser Arg Leu Thr Ile Cys Glu Phe End 3350                                                                3400
TGG GAC AGG GAG GAC GCT CTC CTT GTC GGC CTC CAT CCT GAG GCT CCA CTT GGT

EcoRI          3450
CTG TGA GAT GCT AGA ACT CCC TTT CAA CAG AAT TCC ACT TGT GGC TAT TGG GAC

3500
TGG AGG CAC CCT TAG CCA CTT CAT TCC TCT GAT GGG CCC TGA CTC TTC CCC ATA

3550
ATC ACT CGA CCA GCC TTG ACA CTC CCC TTG CAA ACT CTC CCA GCA CTG CAC CCC

3600
AGG CAG CCA CTC TTA GCC TTG GCC TTC GAC ATG AGA TGG AGC CCT CCT TAT TCC

3650
CCA TCT GGT CCA GTT CCT TCA CTT ACA GAT GGC AGC AGT GAG GTC TTG GGG TAG

3700
AAG GAC CCT CCA AAG TCA CAC AAA GTG CCT GCC TCC TGG TCC CCT CAG CTC TCT

3750
CTC TGC AAC CCA GTG CCA TCA GGA TGA GCA ATC CTG GCC AAG CAT AAT GAC AGA

3800
GAG AGG CAG ACT TCG GGG AAG CCC TGA CTG TGC AGA GCT AAG GAC ACA GTG GAG

3850
ATT CTC TGG CAC TCT GAG GTC TCT GTG GCA GGC CTG GTC AGG CTC TCC ATG AGG
```

FIG. 3-6

```
                3900
TTA GAA GGC CAG GTA GTT GTT CCA GCA GGG TGG TGG CCA AGC CAA CCC CAT GAT

3950
TGA TGT GTA CGA TTC ACT CCT TTG AGT CTT TGA ATG GCA ACT CAG CCC CCT GAC 4000                                                                4050
CTG AAG ACA GCC AGC CTA GGC CTC TAG GTG ACC TAG AGC CGC CTT CAG ATG TGA

4100
CCC GAG TAA CTT TCA ACT GAT GAA CAA ATC TGC ACC CTA CTT CAG ATT TCA GTG

4150
GGC ATT CAC ATC ACC CCC ACA CCA CTG GCT CTG CTT TCT CCT TTC ATT AAT CCA

4200
TTC ACC CAG ATA TTT CAT TAA AAT TAT CAC GTG CCA GGT CTT AGG ATA TGT CGT

4250
GGG GTG GGC AAG GTA ATC AGT GAC AGT TGA AGA TTT TTT TTT CCC AGA GCT TAT

4300
GTC TTC ATC TGT GAA ATG GGA ATA AGA TAC TTG TTG CTG TCA CAG TTA TTA CCA

4350
TCC CCC CAG CTA CCA AAA TTA CTA CCA GAA CTG TTA CTA TAC ACA GAG GCT ATT

4400
GAC TGA GCA CCT ATC ATT TGC CAA GAA CCT TGA CAA GCA CTT CTA ATA CAG CAT

4450
ATT ATG TAC TAT TCA ATC TTC ACA CAA TGT CAC GGG ACC AGT ATT GTT TCC TCA

4500    HindIII
TTT TTT ATA AGG ACA CTG AAG CTT GGA GGA GTT AAA TGT TTT GAG TAT TAT TCC 4550        BamHI
AGA GAG CAA GTG GCA GAG GCT GGA TCC
```

```
                                      27                                                    54
GGG GGG GGG GGG GGG GGG GTA ATG ACA GTA GGA GAG AAG GTC TTC TCC AGC AAT
                            Val MET Tnr Val Gly Glu Lys Val Pne Ser Ser Asn 81                                                   108
GGG CAG TCC ATC ACT TTT GAT GCC ATT CAG GAG GCA TGT GCC AGA GCA GGC GGC
Gly Gln Ser Ile Tnr Pne Aso Ala Ile Gln Glu Ala Cys Ala Arg Ala Gly Gly 135                                                   162
CGC ATT GCT GTC CCA AGG AAT CCA GAG GAA AAT GAG GCC ATT GCA AGC TTC GTG
Arg Ile Ala Val Pro Arg Asn Pro Glu Glu Asn Glu Ala Ile Ala Ser Pne Val 189                                                   216
AAG AAG TAC AAC ACA TAT GCC TAT GTA GGC CTG ACT GAG GGT CCC AGC CCT GGA
Lys Lys Tyr Asn Tnr Tyr Ala Tyr Val Gly Leu Tnr Glu Gly Pro Ser Pro Gly 243                                                   270
GAC TTC CGC TAC TCA GAC GGG ACC CCT GTA AAC TAC ACC AAC TGG TAC CGA GGG
Aso Pne Arg Tyr Ser Aso Gly Tnr Pro Val Asn Tyr Tnr Asn Tro Tyr Arg Gly 297                                                   324
GAG CCC GCA GGT CGG GGA AAA GAG CAG TGT GTG GAG ATG TAC ACA GAT GGG CAG
Glu Pro Ala Gly Arg Gly Lys Glu Gln Cys Val Glu MET Tyr Tnr Aso Gly Gln 351                                                   378
TGG AAT GAC AGG AAC TGC CTG TAC TCC CGA CTG ACC ATC TGT GAG TTC TGA GAG
Tro Asn Aso Arg Asn Cys Leu Tyr Ser Arg Leu Tnr Ile Cys Glu Pne  .

405                                                   432
GCA TTT AGG CCA TGG GAC AGG GAG GAC GCT CTC CTT GTC GGC CTC CAT CCT GAG 459                                                   486
GCT CCA CTT GGT CTG TGA GAT GCT AGA ACT CCC TTT CAA CAG AAT TCC ACT TGT 513                                                   540
GGC TAT TGG GAC TGG AGG CAC CCT TAG CCA CTT CAT TCC TCT GAT GGG CCC TGA 567                                                   594
CTC TTC CCC ATA ATC ACT CGA CCA GCC TTG ACA CTC CCC TTG CAA ACT CTC CCA 621                                                   648
GCA CTG CAC CCC AGG CAG CCA CTC TTA GCC TTG GCC TTC GAC ATG AGA TGG AGC 675                                                   702
CCT CCT TAT TCC CCA TCT GGT CCA GTT CCT TCA CTT ACA GAT GGC AGC AGT GAG 729                                                   756
GTC TTG GGG TAG AAG GAC CCT CCA AAG TCA CAC AAA GTG CCT GCC TCC TGG TCC 783                                                   810
CCT CAG CTC TCT CTC TGC AAC CCA GTG CCA TCA GGA TGA GCA ATC CTG GCC AAG 837                                                   864
CAT AAT GAC AGA GAG AGG CAG ACT TCG GGG AAG CCC TGA CTG TGC AGA GCT AAG 891                                                   918
GAC ACA GTG GAG ATT CTC TGG CAC TCT GAG GTC TCT GTG GCA GGC CTG GTC AGG
```

FIG. 5-1

Figure 5, Page 2

```
                945
CTC TCC ATG AGG TTA GAA GGC CAG GTA GTT CCA GCA GGG TGG CCA AGC
                                                              972
                999                                          1026
CAA CCC CAT GAT TGA TGT GTA CGA TTC ACT CCT TTG AGT CTT TGA ATG GCA ACT
                1053                                         1080
CAG CCC CCT GAC CTG AAG ACA GCC AGC CTA GGC CTC TAG GTG ACC TAG AGC CGC
                1107                                         1134
CTT CAG ATG TGA CCC GAG TAA CTT TCA ACT GAT GAA CAA ATC TGC ACC CTA CTT
                1161                                         1188
CAG ATT TCA GTG GGC ATT CAC ATC ACC CCC ACA CCA CTG GCT CTG CTT TCT CCT
                1215                                         1242
TTC ATT AAT CCA TTC ACC CAG ATA TTT CAT TAA AAT TAT CAC GTG CCA GGT CTT
                1269                                         1296
AGG ATA TGT CGT GGG GTG GGC AAG GTA ATC AGT GAC AGT TGA AGA TTT TTT TTT
                1323
CCC AGA GCT TAT GTC TTC CCC CCC CCC CCC CC
```

Human SP₁₈ cDNA #3

```
                                                                          50
    GAATTCGGGTGCC ATG GCT GAG TCA CAC CTG CTG CAG TGG CTG CTG CTG CTG CTG
                  MET Ala Glu Ser His Leu Leu Gln Trp Leu Leu Leu Leu Leu
                  -200
                                                                         100
CCC ACG CTC TGT GGC CCA GGC ACT GCT GCC TGG ACC ACC TCA TCC TTG GCC TGT
Pro Thr Leu Cys Gly Pro Gly Thr Ala Ala Trp Thr Thr Ser Ser Leu Ala Cys
                                                         150
GCC CAG GGC CCT GAG TTC TGG TGC CAA AGC CTG GAG CAA GCA TTG CAG TGC AGA
Ala Gln Gly Pro Glu Phe Trp Cys Gln Ser Leu Glu Gln Ala Leu Gln Cys Arg
                                             200
GCC CTA GGG CAT TGC CTA CAG GAA GTC TGG GGA CAT GTG GGA GCC GAT GAC CTA
Ala Leu Gly His Cys Leu Gln Glu Val Trp Gly His Val Gly Ala Asp Asp Leu
                                 250
TGC CAA GAG TGT GAG GAC ATC GTC CAC ATC CTT AAC AAG ATG GCC AAG GAG GCC
Cys Gln Glu Cys Glu Asp Ile Val His Ile Leu Asn Lys MET Ala Lys Glu Ala
                         300
ATT TTC CAG GAC ACG ATG AGG AAG TTC CTG GAG CAG GAG TGC AAC GTC CTC CCC
Ile Phe Gln Asp Thr MET Arg Lys Phe Leu Glu Gln Glu Cys Asn Val Leu Pro
                 350
TTG AAG CTG CTC ATG CCC CAG TGC AAC CAA GTG CTT GAC GAC TAC TTC CCC CTG
Leu Lys Leu Leu MET Pro Gln Cys Asn Gln Val Leu Asp Asp Tyr Phe Pro Leu
         400
GTC ATC GAC TAC TTC CAG AAC CAG ATT GAC TCA AAC GGC ATC TGT ATG CAC CTG
Val Ile Asp Tyr Phe Gln Asn Gln Ile Asp Ser Asn Gly Ile Cys MET His Leu
             450
GGC CTG TGC AAA TCC CGG CAG CCA GAG CCA GAG CAG GAG CCA GGG ATG TCA GAC
Gly Leu Cys Lys Ser Arg Gln Pro Glu Pro Glu Gln Glu Pro Gly MET Ser Asp
         500
CCC CTG CCC AAA CCT CTG CGG GAC CCT CTG CCA GAC CCT CTG CTG GAC AAG CTC
Pro Leu Pro Lys Pro Leu Arg Asp Pro Leu Pro Asp Pro Leu Leu Asp Lys Leu
     550
GTC CTC CCT GTG CTG CCC GGG GCC CTC CAG GCG AGG CCT GGG CCT CAC ACA CAG
Val Leu Pro Val Leu Pro Gly Ala Leu Gln Ala Arg Pro Gly Pro His Thr Gln
 600                                                                     650
GAT CTC TCC GAG CAG CAA TTC CCC ATT CCT CTC CCC TAT TGC TGG CTC TGC AGG
Asp Leu Ser Glu Gln Gln Phe Pro Ile Pro Leu Pro Tyr Cys Trp Leu Cys Arg
                         -1  +1
                                                                     700
GCT CTG ATC AAG CGG ATC CAA GCC ATG ATT CCC AAG GGT GCG CTA CGT GTG GCA
Ala Leu Ile Lys Arg Ile Gln Ala MET Ile Pro Lys Gly Ala Leu Arg Val Ala
```

FIG. 6-1

Figure 6, page 2

```
                                                                750
GTG GCC CAG GTG TGC CGC GTG GTA CCT CTG GTG GCG GGC GGC ATC TGC CAG TGC
Val Ala Gln Val Cys Arg Val Val Pro Leu Val Ala Gly Gly Ile Cys Gln Cys
                                                        800
CTG GCT GAG CGC TAC TCC GTC ATC CTG CTC GAC ACG CTG CTG GGC CGC ATG CTG
Leu Ala Glu Arg Tyr Ser Val Ile Leu Leu Asp Thr Leu Leu Gly Arg MET Leu
                                                850
CCC CAG CTG GTC TGC CGC CTC GTC CTC CGG TGC TCC ATG GAT GAC AGC GCT GGC
Pro Gln Leu Val Cys Arg Leu Val Leu Arg Cys Ser MET Asp Asp Ser Ala Gly
                                        900
CCA AGG TCG CCG ACA GGA GAA TGG CTG CCG CGA GAC TCT GAG TGC CAC CTC TGC
Pro Arg Ser Pro Thr Gly Glu Trp Leu Pro Arg Asp Ser Glu Cys His Leu Cys
                                950
ATG TCC GTG ACC ACC CAG GCC GGG AAC AGC AGC GAG CAG GCC ATA CCA CAG GCA
MET Ser Val Thr Thr Gln Ala Gly Asn Ser Ser Glu Gln Ala Ile Pro Gln Ala
                        1000
ATG CTC CAG GCC TGT GTT GGC TCC TGG CTG GAC AGG GAA AAG TGC AAG CAA TTT
MET Leu Gln Ala Cys Val Gly Ser Trp Leu Asp Arg Glu Lys Cys Lys Gln Phe
                1050
GTG GAG CAG CAC ACG CCC CAG CTG CTG ACC CTG GTG CCC AGG GGC TGG GAT GCC
Val Glu Gln His Thr Pro Gln Leu Leu Thr Leu Val Pro Arg Gly Trp Asp Ala
        1100
CAC ACC ACC TGC CAG GCC CTC GGG GTG TGT GGG ACC ATG TCC AGC CCT CTC CAG
His Thr Thr Cys Gln Ala Leu Gly Val Cys Gly Thr MET Ser Ser Pro Leu Gln
        1150
TGT ATC CAC AGC CCC GAC CTT TGA TGAGAACTCAG CTGTCCAGAA AAAGACACGT CCTTT
Cys Ile His Ser Pro Asp Leu End
                        181
1200                                                    1250
AAAAT GCTGCAGTAT GGCCAGACAG TGGTGGCTCA CACCTGCAAT CCCAGCACCT TAGGAGGCCG
        1275
AGGCAGGAGG ATCC
```

FIG. 6-2

```
                                      ggctctttctagg tataaa cactgcttgccgcgctgcactccaCCACG
```

```
                                                                         ◄────MT-IIA
CCTCCTCCAAGTCCCAGCGAACCCGCGTGCAACCTGTCCCGACTCTAGCCGCCTCTTCAGCTCAC GGATC
```

```
2    HS────►                                                     50
AAT TCC AAG TCG CTG GAG GCT CTG TGT GTG GGA GCA GCG ACT GGA CCC AGA GCC

100
ATG TGG CTG TGC CCT CTG GCC CTC AAC CTC ATC TTG ATG GCA GCC TCT GGT GCT
MET Trp Leu Cys Pro Leu Ala Leu Asn Leu Ile Leu MET Ala Ala Ser Gly Ala
-20
                                                         150
GTG TGC GAA GTG AAG GAC GTT TGT GTT GGA AGC CCT GGT ATC CCC GGC ACT CCT
Val Cys Glu Val Lys Asp Val Cys Val Gly Ser Pro Gly Ile Pro Gly Thr Pro
          1
                                              200
GGA TCC CAC GGC CTG CCA GGC AGG GAC GGG AGA GAT GGT GTC AAA GGA GAC CCT
Gly Ser His Gly Leu Pro Gly Arg Asp Gly Arg Asp Gly Val Lys Gly Asp Pro
                                    *                   *              *
                       250
GGC CCT CCA GGC CCC ATG GGT CCA CCT GGA GAA ATG CCA TGT CCT CCT GGA AAT
Gly Pro Pro Gly Pro MET Gly Pro Pro Gly Glu MET Pro Cys Pro Pro Gly Asn

300
GAT GGG CTG CCT GGA GCC CCT GGT ATC CCT GGA GAG TGT GGA GAG AAG GGG GAG
Asp Gly Leu Pro Gly Ala Pro Gly Ile Pro Gly Glu Cys Gly Glu Lys Gly Glu

350
CCT GGC GAG AGG GGC CCT CCA GGG CTT CCA GCT CAT CTA GAT GAG GAG CTC CAA
Pro Gly Glu Arg Gly Pro Pro Gly Leu Pro Ala His Leu Asp Glu Glu Leu Gln

400
GCC ACA CTC CAC GAC TTT AGA CAT CAA ATC CTG CAG ACA AGG GGA GCC CTC AGT
Ala Thr Leu His Asp Phe Arg His Gln Ile Leu Gln Thr Arg Gly Ala Leu Ser

450
CTG CAG GGC TCC ATA ATG ACA GTA GGA GAG AAG GTC TTC TCC AGC AAT GGG CAG
Leu Gln Gly Ser Ile MET Thr Val Gly Glu Lys Val Phe Ser Ser Asn Gly Gln
```

FIG. 7-1.

```
                    500
TCC ATC ACT TTT GAT GCC ATT CAG GAG. GCA TGT GCC AGA GCA GGC GGC CGC ATT
Ser Ile Thr Phe Asp Ala Ile Gln Glu Ala Cys Ala Arg Ala Gly Gly Arg Ile

550
GCT GTC CCA AGG AAT CCA GAG GAA AAT GAG GCC ATT GCA AGC TTC GTG AAG AAG
Ala Val Pro Arg Asn Pro Glu Glu Asn Glu Ala Ile Ala Ser Phe Val Lys Lys 600                                                             650
TAC AAC ACA TAT GCC TAT GTA GGC CTG ACT GAG GGT CCC AGC CCT GGA GAC TTC
Tyr Asn Thr Tyr Ala Tyr Val Gly Leu Thr Glu Gly Pro Ser Pro Gly Asp Phe

700
CGC TAC TCA GAC GGG ACC CCT GTA AAC TAC ACC AAC TGG TAC CGA GGG GAG CCC
Arg Tyr Ser Asp Gly Thr Pro Val Asn Tyr Thr Asn Trp Tyr Arg Gly Glu Pro

750
GCA GGT CGG GGA AAA GAG CAG TGT GTG GAG ATG TAC ACA GAT GGG CAG TGG AAT
Ala Gly Arg Gly Lys Glu Gln Cys Val Glu MET Tyr Thr Asp Gly Gln Trp Asn

800
GAC AGG AAC TGC CTG TAC TCC CGA CTG ACC ATC TGT GAG TTC TGA GAG GCA TTT
Asp Arg Asn Cys Leu Tyr Ser Arg Leu Thr Ile Cys Glu Phe End

850
AGG CCA TGG GAC AGG GAG GAC GCT CTC TGG CCT CCA TCC TGA GGC TCC ACT TGG

←――――HS    900           ApoA1――――→
TCT GTG AGA TGC TAG AAC TCC CTT TCA ACA GAATTGATCCCT GCTGCCCGTGCTGGAGA

GCTTCAAGGTCAGCTTCCTGAGCGCTCTCGAGGAGTACACTAAGAAGCTCAACACCCAGTGAGGCGCCCGC

CGCCGCCCCCCTTCCCGGTGCTCAGAATAAACGTTTCCAAAGTGgga
```

FIG. 7-2

```
                                              ggctctttctagc tataaa cactgct tgccgcgctgcactccaCCACGCCTCCTCCAAGTCCCAGCGAACCCGCGTGCAACCTGTCCCGACTCTAGC ←———MT-IIA       2      HS———→
         CGCCTCTTCAGCTCAC  GGATCAATTC  CCAAG TCG CTG GAG GCT CTG TGT GTG GGA GCA GCG ACT GGA CCC AGA GCC ATG TGG CTG TGC CCT CTG GCC CTC AAC CTC ATC TTG
                        MET Trp Leu Cys Pro Leu Ala Leu Asn Leu Ile Leu
                        -20
     100
ATG GCA GCC TCT GGT GCT GTG TGC GAA GTG AAG GAC GTT TGT GTT GGA AGC CCT
MET Ala Ala Ser Gly Ala Val Cys Glu Val Lys Asp Val Cys Val Gly Ser Pro
                                 1
        150     ←———HS      PSAP———→
GGT ATC CCC GGC ACT CCT GGA TCC CAC GGC CTG CCA GGC AGG GAC GGG AGA GAT
Gly Ile Pro Gly Thr Pro Gly Ser His Gly Leu Pro Gly Arg Asp Gly Arg Asp 1200
GGT CTC AAA GGA GAC CCT GGC CCT CCA G gtac tgt gct gca gac ccc acc ctc
Gly Leu Lys Gly Asp Pro Gly Pro Pro G 1250
agc tga gga cac aga ccc ctt ttc agg agg ccc atc tgt cca ggc ccc tag gct 1300                                                                1350
gtg ggc cat agt gag ctg ggg gct ata gta agc tgg gtg gga ctt cag tct gca 1400
ggg ctg gtg ggt tcc tgg ggc cct tat gat ggc gca tcc tgg aga gtc tgt cct 1450
cat agt gcc cac gga gtg ata gag tga tag ctg agc cag ccc tgg tga taa tgg 1500
gca tcg agt ctc act agc tcc aac cag ttg tgg gtg aca gat cct aca cat cca
```

FIG. 8-1

```
                                              1550
tgt ctc ttt tct ctg cag GC CCC ATG GGT CCA CCT GGA GAA ATG CCA TGT CCT
                        ly Pro Met Gly Pro Pro Gly Glu Met Pro Cys Pro 1600
CCT GGA AAT GAT GGG CTG CCT GGA GCC CCT GGT ATC CCT GGA GAG TGT GGA GAG
Pro Gly Asn Asp Gly Leu Pro Gly Ala Pro Gly Ile Pro Gly Glu Cys Gly Glu 1650
AAG GGG GAG CCT GGC GAG AGG GGC CCT CCA G gtg agc agg gtg ggg cag gtg ggc
Lys Gly Glu Pro Gly Glu Arg Gly Pro Pro G 1700
agt gga aac atg ggc aca gcg acc ctg aag tca gtt aca cgg gga tga tgg gga 1750
tca gac aaa ccc tac agg ttc ccc aag ggc att tgg ctc aac cta agt aag aga 1800
gga taa gct tga ggg aga aag ctg agg tgt ctg ggg agt gtg gtc aca att cag 1850
gga aag gca ggt gtg gga agt cct ccg tgc ctc atg acc acc gat ggg gac aca 1900
ctg agt cag gtg tgg gat gag gga cag cac tgg gag gca ggg gag gca tgt cct 1950
ggg atg gag gcc ctg ggg ctg tct gaa ggg tga atg cgg acg agg cat cca gac 2000                                                             2050
aga cgg tgt gat cag gag ccc cac aga cag agg gga act ttg aag ctc aga gcg 2100
gta agc aag tcc atc agg gca gtg cag aga gca tca tgc ttg ccc ttc ggt cgg 2150
agg gtg cgg gag agg gac ttg ccc cac aga ggc ggg cag aca gaa ccc ctc gag 2200
gac aag agc agg aaa gag gac aag ggg tgg ggg tct cag cag ggg caa ggc ttc
```

FIG. 8-2

```
                                         2250
act aaa gaa tag ggg acc acg ggt ctg aga cac act gga atc ttg tgg acc ctc 2300
tga gcc tag gtc tgg tgg cgc cta aca gca atg aaa ggg cag agt tcc agg att 2350
gca gat ggc aaa aca cct cgt ggc agc aag tgg gag tct tca ctg gcc tgc ccc 2400
tcc ttc tgt gtg ggg cac tct cca cag GG CTT CCA GCT CAT CTA GAT GAG GAG
                                    ly Leu Pro Ala His Leu Asp Glu Glu 2450
CTC CAA GCC ACA CTC CAC GAC TTT AGA CAT CAA ATC CTG CAG ACA AGG GGA G gta
Leu Gln Ala Thr Leu His Asp Phe Arg His Gln Ile Leu Gln Thr Arg Gly A 2500
agg gga ccc cct ggg ctc acg ggg tag gag ttt ccc aca aat tcc cct cat tct 2550
cag cac cag ctt cta gaa cat aga gat tac aaa tag gca tgc aca tgc agg tct 2600
tgg gga aag gaa ttg acg ctt gct ttt ctt gat gtc ttt tga atg gcc cag agg 2650                                                              2700
aga cag aag cag aca caa ttc act tcc ccg att tca tag gaa agc aag ttc tct 2750
atc tgc ctt gct ttc cac tga att cac agg aaa ttg cac cat ttc tgg caa taa 2800
gta att gtt act tag gtg aat gaa taa atg gag gag agt cta aaa gtg aat tta 2850
gaa aac tgc aat tgg aag agg aag aga aga cac aga gag agg cag aga tgg aga 2900
gac tgg gga gaa tct ggt agc aga gac ccc agg tga ggg agg tgg ctt aga gac

FIG. 8-3
```

```
                                         2950
aaa gtg gtc agt ggc ctg acc cgg act cct ctg ctc tcag CC CTC AGT CTG CAG
                                                     la Leu Ser Leu Gln 3000
GGC TCC ATA ATG ACA GTA GGA GAG AAG GTC TTC TCC AGC AAT GGG CAG TCC ATC
Gly Ser Ile Met Thr Val Gly Glu Lys Val Phe Ser Ser Asn Gly Gln Ser Ile 3050
ACT TTT GAT GCC ATT CAG GAG GCA TGT GCC AGA GCA GGC GGC CGC ATT GCT GTC
Thr Phe Asp Ala Ile Gln Glu Ala Cys Ala Arg Ala Gly Gly Arg Ile Ala Val 3100
CCA AGG AAT CCA GAG GAA AAT GAG GCC ATT GCA AGC TTC GTG AAG AAG TAC AAC
Pro Arg Asn Pro Glu Glu Asn Glu Ala Ile Ala Ser Phe Val Lys Lys Tyr Asn 3150
ACA TAT GCC TAT GTA GGC CTG ACT GAG GGT CCC AGC CCT GGA GAC TTC CGC TAC
Thr Tyr Ala Tyr Val Gly Leu Thr Glu Gly Pro Ser Pro Gly Asp Phe Arg Tyr 3200
TCA GAC GGG ACC CCT GTA AAC TAC ACC AAC TGG TAC CGA GGG GAG CCC GCA GGT
Ser Asp Gly Thr Pro Val Asn Tyr Thr Asn Trp Tyr Arg Gly Glu Pro Ala Gly 3250
CGG GGA AAA GAG CAG TGT GTG GAG ATG TAC ACA GAT GGG CAG TGG AAT GAC AGG
Arg Gly Lys Glu Gln Cys Val Glu Met Tyr Thr Asp Gly Gln Trp Asn Asp Arg 3300
AAC TGC CTG TAC TCC CGA CTG ACC ATC TGT GAG TTC TGA GAG GCA TTT AGG CCA
Asn Cys Leu Tyr Ser Arg Leu Thr Ile Cys Glu Phe End 3350                                                            3400
TGG GAC AGG GAG GAC GCT CTC CTT GTC GGC CTC CAT CCT GAG GCT CCA CTT GGT ◄────PSAP   3435       ApoAI────►
CTG TGA GAT GCT AGA ACT CCC TTT CAA CA  GAATTGATCCCT GCTGCCCGTGCTGGAGA

GAGCTTCAAGGTCAGCTTCCTGAGCGCTCTCGAGGAGTACACTAAGAAGCTCAACACCCAGTGAGGCGCCC

GCCGCCGCCCCCCTTCCCGGTGCTCAG AATAAA CGTTTCCAAAGTGggaagcagcttctttct...
```

FIG. 8-4

```
                                                              ggctctttc
tagctataaacactgcttgccgcgctgcactccaCCACGCCTCCTCCAAGTCCCAGCGAACCCGCGTGCAA ◄────MT-IIA     951    PSAP────►
CCTGTCCCGACTCTAGCCGCCTCTTCAGCTCAC  GGATCAGTC   C TGA CAG AGC ACA GTG GGG 1000
GAG ATG TTG GCA GAG GTG GCA GAT GGG CTC ACG GCC ATC CCT CCT GCA GGA GCA
    MET Leu Ala Glu Val Ala Asp Gly Leu Thr Ala Ile Pro Pro Ala Gly Ala
    -43

1050
GCG ACT GGA CCC AGA GCC ATG TGG CTG TGC CCT CTG GCC CTC AAC CTC ATC TTG
Ala Thr Gly Pro Arg Ala MET Trp Leu Cys Pro Leu Ala Leu Asn Leu Ile Leu

1100
ATG GCA GCC TCT GGT GCT GTG TGC GAA GTG AAG GAC GTT TGT GTT GGA AGC CCT
MET Ala Ala Ser Gly Ala Val Cys Glu Val Lys Asp Val Cys Val Gly Ser Pro
                                 1

1150
GGT ATC CCC GGC ACT CCT GGA TCC CAC GGC CTG CCA GGC AGG GAC GGG AGA GAT
Gly Ile Pro Gly Thr Pro Gly Ser His Gly Leu Pro Gly Arg Asp Gly Arg Asp

1200
GGT CTC AAA GGA GAC CCT GGC CCT CCA G gtac tgt gct gca gac ccc acc ctc
Gly Leu Lys Gly Asp Pro Gly Pro Pro G 1250
agc tga gga cac aga ccc ctt ttc agg agg ccc atc tgt cca ggc ccc tag gct 1300                                                                1350
gtg ggc cat agt gag ctg ggg gct ata gta agc tgg gtg gga ctt cag tct gca 1400
ggg ctg gtg ggt tcc tgg ggc cct tat gat ggc gca tcc tgg aga gtc tgt cct 1450
cat agt gcc cac gga gtg ata gag tga tag ctg agc cag ccc tgg tga taa tgg 1500
gca tcg agt ctc act agc tcc aac cag ttg tgg gtg aca gat cct aca cat cca
```

FIG. 9-1

```
                                    1550
tgt ctc ttt tct ctg cag GC CCC ATG GGT CCA CCT GGA GAA ATG CCA TGT CCT
                         ly Pro MET Gly Pro Pro Gly Glu MET Pro Cys Pro 1600
CCT GGA AAT GAT GGG CTG CCT GGA GCC CCT GGT ATC CCT GGA GAG TGT GGA GAG
Pro Gly Asn Asp Gly Leu Pro Gly Ala Pro Gly Ile Pro Gly Glu Cys Gly Glu 1650
AAG GGG GAG CCT GGC GAG AGG GGC CCT CCA G GTG AGC AGG GTG GGG CAG GTG GGC
Lys Gly Glu Pro Gly Glu Arg Gly Pro Pro G

1700
AGT GGA AAC ATG GGC ACA GCG ACC CTG AAG TCA GTT ACA CGG GGA TGA TGG GGA

1750
TCA GAC AAA CCC TAC AGG TTC CCC AAG GGC ATT TGG CTC AAC CTA AGT AAG AGA

1800
GGA TAA GCT TGA GGG AGA AAG CTG AGG TGT CTG GGG AGT GTG GTC ACA ATT CAG

1850
GGA AAG GCA GGT GTG GGA AGT CCT CCG TGC CTC ATG ACC ACC GAT GGG GAC ACA

1900
CTG AGT CAG GTG TGG GAT GAG GGA CAG CAC TGG GAG GCA GGG GAG GCA TGT CCT

1950
GGG ATG GAG GCC CTG GGG CTG TCT GAA GGG TGA ATG CGG ACG AGG CAT CCA GAC 2000                                                             2050
AGA CGG TGT GAT CAG GAG CCC CAC AGA CAG AGG GGA ACT TTG AAG CTC AGA GCG

2100
GTA AGC AAG TCC ATC AGG GCA GTG CAG AGA GCA TCA TGC TTG CCC TTC GGT CGG

2150
AGG GTG CGG GAG AGG GAC TTG CCC CAC AGA GGC GGG CAG ACA GAA CCC CTC GAG

2200
GAC AAG AGC AGG AAA GAG GAC AAG GGG TGG GGG TCT CAG CAG GGG CAA GGC TTC
```

FIG. 9-2

```
                                    2250
ACT AAA GAA TAG GGG ACC ACG GGT CTG AGA CAC ACT GGA ATC TTG TGG ACC CTC

2300
TGA GCC TAG GTC TGG TGG CGC CTA ACA GCA ATG AAA GGG CAG AGT TCC AGG ATT

2350
GCA GAT GGC AAA ACA CCT CGT GGC AGC AAG TGG GAG TCT TCA CTG CCT GCC CCC

2400
TCC TTC TGT GTG GGG CAC TCT CCA CAG GG CTT CCA GCT CAT CTA GAT GAG GAG
                                         ly Leu Pro Ala His Leu Asp Glu Glu

2450
CTC CAA GCC ACA CTC CAC GAC TTT AGA CAT CAA ATC CTG CAG ACA AGG GGA G TA
Leu Gln Ala Thr Leu His Asp Phe Arg His Gln Ile Leu Gln Thr Arg Gly A

2500
AGG GGA CCC CCT GGG CTC ACG GGG TAG GAG TTT CCC ACA AAT TCC CCT CAT TCT

2550
CAG CAC CAG CTT CTA GAA CAT AGA GAT TAC AAA TAG GCA TGC ACA TGC AGG TCT

2600
TGG GGA AAG GAA TTG ACG CTT GCT TTT CTT GAT GTC TTT TGA ATG GCC CAG AGG 2650                                                                2700
AGA CAG AAG CAG ACA CAA TTC ACT TCC CCG ATT TCA TAG GAA AGC AAG TTC TCT

2750
ATC TGC CTT GCT TTC CAC TGA ATT CAC AGG AAA TTG CAC CAT TTC TGG CAA TAA

2800
GTA ATT GTT ACT TAG GTG AAT GAA TAA ATG GAG GAG AGT CTA AAA GTG AAT TTA

2850
GAA AAC TGC AAT TGG AAG AGG AAG AGA AGA CAC AGA GAG AGG CAG AGA TGG AGA

2900
GAC TGG GGA GAA TCT GGT AGC AGA GAC CCC AGG TGA GGG AGG TGG CTT AGA GAC
```

FIG. 9-3

```
                                       2950
CAA GTG GTC AGT GGC CTG ACC CGG ACT CCT CTG CTC TCAG CC CTC AGT CTG CAG
                                                       la  Leu Ser Leu Gln

3000
GGC TCC ATA ATG ACA GTA GGA GAG AAG GTC TTC TCC AGC AAT GGG CAG TCC ATC
Gly Ser Ile MET Thr Val Gly Glu Lys Val Phe Ser Ser Asn Gly Gln Ser Ile

3050
ACT TTT GAT GCC ATT CAG GAG GCA TGT GCC AGA GCA GGC GGC CGC ATT GCT GTC
Thr Phe Asp Ala Ile Gln Glu Ala Cys Ala Arg Ala Gly Gly Arg Ile Ala Val

3100
CCA AGG AAT CCA GAG GAA AAT GAG GCC ATT GCA AGC TTC GTG AAG AAG TAC AAC
Pro Arg Asn Pro Glu Glu Asn Glu Ala Ile Ala Ser Phe Val Lys Lys Tyr Asn

3150
ACA TAT GCC TAT GTA GGC CTG ACT GAG GGT CCC AGC CCT GGA GAC TTC CGC TAC
Thr Tyr Ala Tyr Val Gly Leu Thr Glu Gly Pro Ser Pro Gly Asp Phe Arg Tyr

3200
TCA GAC GGG ACC CCT GTA AAC TAC ACC AAC TGG TAC CGA GGG GAG CCC GCA GGT
Ser Asp Gly Thr Pro Val Asn Tyr Thr Asn Trp Tyr Arg Gly Glu Pro Ala Gly

3250
CGG GGA AAA GAG CAG TGT GTG GAG ATG TAC ACA GAT GGG CAG TGG AAT GAC AGG
Arg Gly Lys Glu Gln Cys Val Glu MET Tyr Thr Asp Gly Gln Trp Asn Asp Arg

3300
AAC TGC CTG TAC TCC CGA CTG ACC ATC TGT GAG TTC TGA GAG GCA TTT AGG CCA
Asn Cys Leu Tyr Ser Arg Leu Thr Ile Cys Glu Phe End 3350                                                               3400
TGG GAC AGG GAG GAC GCT CTC CTT GTC GGC CTC CAT CCT GAG GCT CCA CTT GGT

◄──────PSAP   3435      ApoAI──────►
           CTG TGA GAT GCT AGA ACT CCC TTT CAA CA  GAATTGATCCCT  GCTGCCCGTGCTGGAGA

GAGCTTCAAGGTCAGCTTCCTGAGCGCTCTCGAGGAGTACACTAAGAAGCTCAACACCCAGTGAGGCGCCC

GCCGCCGCCCCCCTTCCCGGTGCTCAG AATAAA CGTTTCCAAAGTGggaagcagcttctttct...
```

FIG. 9-4

RECOMBINANT DNA SEQUENCE ENCODING ALVEOLAR SURFACTANT PROTEIN

CROSS-REFERENCE TO RELATED APPLICATION

This application is a continuation-in-part of U.S. patent application Ser. No. 808,843, filed 13 Dec. 1985 which is a continuation-in-part of U.S. patent application Ser. No. 680,358, filed 11 Dec. 1984 now U.S. Pat. No. 4,659,805.

TECHNICAL FIELD

The invention relates to the field of recombinant protein production. More specifically it relates to the production of alveolar surfactant protein (ASP) which is useful in the management of certain respiratory diseases.

BACKGROUND ART

The human lung is composed of a large number of small sacs or alveoli in which gases are exchanged between the blood and the air spaces of the lung. In healthy individuals, this exchange is mediated by the presence of a protein containing surfactant complex which is synthesized in the microsomal membranes of type II alveolar cells. In the absence of adequate levels of this complex, a lung cannot properly function—i.e., the alveoli collapse during exhalation, and cannot be subsequently re-inflated by inhaling. Thus, the untreated inability to synthesize this complex may result in death or in severe physical damage.

The best documented instance of inadequate surfactant complex levels occurs in premature infants and infants born after complicated pregnancies, and is widely known as respiratory distress syndrome (RDS). A widely publicized form of this syndrome has been designated hyaline membrane disease, or idiopathic RDS. RDS is currently the leading cause of infant mortality and morbidity in the United States and in other developed countries, and substantial efforts have been directed to diagnosis and treatment. Current treatment has focused on mechanical (pressure) ventilation which, at best, is an invasive stop-gap measure that often results in damage to the lung and other deleterious side effects, including complications such as bronchopulmonary dysplasia, interstitial emphysema and pneumothorax. Mental retardation has also resulted on occasion when this treatment was used (Hallman, M., et al, *Pediatric Clinics of North America* (1982) 29: 1057–1075).

Limited attempts have been made to treat the syndrome by surfactant substitution. This would be a method of choice, as, in general, only one administration is required, and the potential for damage is reduced. For example, Fujwara, et al, *Lancet* (1980) 1: 55 -used a protein-depleted surfactant preparation derived from bovine lungs; the preparation is effective but immunogenic. Hallman, M., et al, *Pediatrics* (1983) 71: 473–482 used a surfactant isolate from human amniotic fluid to treat a limited number of infants with some success. U.S. Pat. No. 4,312,860 to Clements discloses an artificial surfactant which contains no protein and is said to be useful in this approach although no data are shown. In short, surfactant substitution has not been widely used clinically.

The preferred surfactant substitute would be the lung surfactant complex itself. This complex is composed of apoprotein, two phospholipids (dipalmitoyl phosphocholine (DPPC) and phosphatidyl-glycerol (PG)) which are present in major amount, several lipid components present in only very minor amount, and calcium ions. The apoprotein contains proteins having molecular weights of the order of 32,000 daltons and very hydrophobic proteins of the order of about 10,000 daltons (King, R. J. et al, *Am J Physiol* (1973) 224: 788–795). The 32,000 dalton protein is glycosylated and contains hydroxyproline.

A major reason for the limited progress in surfactant replacement therapy has been the lack of availability of the protein portion of the complex. Replacement therapies have focused on attempts to use the lipid components alone, and it appears that the performance of such treatment can be markedly improved by addition of the apoprotein (Hallman, M., et al, *Pediatric Clinics of North America* (1982) (supra)). At present, however, these proteins are available only from normal adult human lung, and from amniotic fluid. Even efficient isolation procedures would not provide an adequate supply. Thus, it would be desirable to have available a method for producing practical quantities of apoprotein for use alone or in conjunction with the saturated phospholipid portion of the complex.

DISCLOSURE OF INVENTION

The invention provides a means for obtaining the apoprotein portion of the lung surfactant complex in quantity and under conditions which permit optimization of its features. The remaining components of the complex, dipalmitoyl phosphocholine and phosphatidylglycerol, along with calcium ions are already readily available. The availability of required quantities of manipulable apoprotein both makes possible research efforts to optimize the form of complex useable in therapy, and opens the possibility for routine replacement therapy of respiratory distress syndrome.

Thus, in one aspect, the invention relates to recombinantly produced mammalian alveolar surfactant protein (ASP). These proteins are mixtures of relatively high molecular weight, relatively water soluble proteins of about 32 kd (32K ASP) and of lower molecular weight, hydrophobic proteins of about 10–20 kd (10K ASP). Both proteins encourage formation of surface tension lowering films when complexed with phospholipid in the presence of calcium ion. The invention further relates to DNA sequences encoding mammalian ASP, including human and canine 32K and 10K ASP, to expression vectors suitable for production of these proteins, to recombinant host cells transformed with these vectors, and to methods of producing the recombinant ASPs and their precursors. In other aspects the invention relates to pharmaceutical compositions containing human ASP and to methods of treating RDS using them.

BRIEF DESCRIPTION OF THE DRAWINGS

FIG. 1 shows the DNA sequence encoding canine 32K ASP, along with the deduced amino acid sequence.

FIG. 2 shows DNA sequence determined for a cDNA encoding canine 10K ASP along with the deduced amino acid sequence.

FIG. 3 shows the nucleotide sequence of the human 32K ASP gene and the deduced amino acid sequence.

FIG. 5 shows the sequence of the 3' terminal portion of human ASP cDNA contained in pHS-6.

FIG. 6 shows DNA sequence determined for a cDNA encoding human 10K ASP along with the deduced amino acid sequence.

FIG. 7 shows the relevant junction and coding sequences of the expression vector pASPc-SV(10).

FIG. 8 shows the relevant junction and coding sequences of the expression vector pASPcg-SV(10).

FIG. 9 shows the relevant junction and coding sequences of the expression vector pMT-Apo:gHS(HinfI/EcoRI).

MODES OF CARRYING OUT THE INVENTION

A. Definitions

Figure 4:
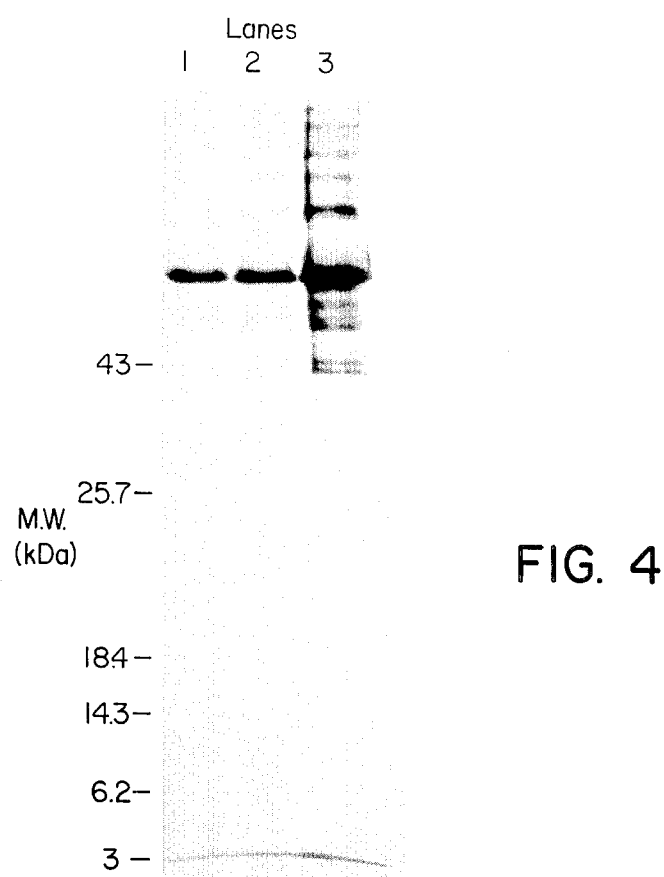
FIG. 4 is an autoradiograph of $^{35}$S-Met-labeled, secreted proteins from CHO cells transfected with λ:gHS-15.

As used herein, "alveolar surfactant protein (ASP)" refers to apoprotein associated with the lung surfactant complex and having ASP activity as defined hereinbelow. The ASP of all species examined appears to comprise one or more components of relatively high molecular weight (of the order of 32 kd) designated herein =K ASP" and one or more quite hydrophobic components of relatively low molecular weight (of the order of 10-20 kd) designated herein "10K ASP". (King, R. J., et al, *J Appl Physiol* (1977) 42: 483–491; Phizackerley, P. J. R., *Biochem J* (1979) 183: 731–736.) These terms refer to the native sequences and to equivalent modifications thereof. For example, human 32K ASP has the amino acid sequence shown in FIG. 3; ASP proteins of approximately 32 kd derived from other species such as dogs, monkeys, or other mammals have substantial degrees of homology with this sequence (see FIG. 1 in connection with the canine ASP). Additional sequence for other specific 32K ASP (canine) and 10K ASP (human and canine) is disclosed hereinbelow.

The recombinant ASP proteins of the invention have amino acid sequences corresponding to those of the native proteins. It is understood that limited modifications may, however, be made without destroying activity, and that only a portion of the entire primary structure may be required. For example, the human ASP 32K recombinant protein of the invention has an amino acid sequence substantially similar to that shown in FIG. 3, but minor modifications of this sequence which do not destroy activity also fall within the definition of 32K human ASP and within definition of the protein claimed as such, as further set forth below. Also included within the definition are fragments of the entire sequence of FIG. 3 which retain activity.

As is the case for all proteins, the ASP proteins can occur in neutral form or in the form of basic or acid addition salts depending on its mode of preparation, or, if in solution, upon its environment. It is well understood that proteins in general, and, therefore, any ASP, in particular, may be found in the form of its acid addition salts involving the free amino groups, or basic salts formed with free carboxyls. Pharmaceutically acceptable salts may, indeed, enhance the functionality of the protein. Suitable pharmaceutically acceptable acid addition salts include those formed from inorganic acids such as, for example, hydrochloric or sulfuric acids, or from organic acids such as acetic or glycolic acid. Pharmaceutically acceptable bases include the alkali hydroxides such as potassium or sodium hydroxides, or such organic bases as piperidine, glucosamine, trimethylamine, choline, or caffeine. In addition, the protein may be modified by combination with other biological materials such as lipids and saccharides, or by side chain modification, such as acetylation of amino groups, phosphorylation of hydroxyl side chains, or oxidation of sulfhydryl groups or other modification of the encoded primary sequence. Indeed, in its native form, the 32K ASP is a glycosylated protein, and certain of the encoded proline residues have been converted to hydroxyproline. It is also found in association with the phospholipds DPPC and PG. Included within the definition of any ASP herein are glycosylated and unglycosylated forms, hydroxylated and non-hydroxylated forms, the apoprotein alone, or in association with lipids, and, in short, any composition of an amino acid sequence substantially similar to that of the native sequences which retains its ability to facilitate the exchange of gases between the blood and lung air spaces and to permit re-inflation of the alveoli.

It is further understood that minor modifications of primary amino acid sequence may result in proteins which have substantially equivalent or enhanced activity as compared to the native sequences. These modifications may be deliberate, as through site-directed mutagenesis, or may be accidental, such as through mutation of hosts which are ASP producing organisms. All of these modifications are included as long as the ASP activity is retained.

"ASP activity" for a protein is defined as the ability, when combined with lipids either alone or in combination with other proteins, to exhibit activity in the in vivo assay of Robertson, B. *Lung* (1980) 158: 57–68. In this assay, the sample to be assessed is administered through an endotrachial tube to fetal rabbits or lambs delivered prematurely by Caesarian section. (These "preemies" lack their own ASP, and are supported on a ventilator.) Measurements of lung compliance, blood gases and ventilator pressure provide indices of activity. Preliminary assessment of activity may also be made by an in vitro assay, for example that of King, R. J., et al, *Am J Physiol* (1972) 223: 715–726, or that illustrated below of Hawgood, et al, which utilizes a straightforward measurement of surface tension at a air-water interface when the protein is mixed with a phospholipid vesicle preparation.

"Operably linked" refers to a juxtaposition wherein the components are configured so as to perform their usual function. Thus, control sequences operably linked to coding sequences are capable of effecting the expression of the coding sequence.

"Control sequence" refers to a DNA sequence or sequences which are capable, when properly ligated to a desired coding sequence, of effecting its expression in hosts compatible with such sequences. Such control sequences include promoters in both procaryotic and eucaryotic hosts, and in procaryotic organisms also include ribosome binding site sequences, and, in eucaryotes, termination signals. Additional factors necessary or helpful in effecting expression may subsequently be identified. As used herein, "control sequences" simply refers to whatever DNA sequence may be required to effect expression in the particular host used.

"Cells" or "recombinant host cells" or "host cells" are often used interchangably as will be clear from the context. These terms include the immediate subject cell, and, of course, the progeny thereof. It is understood that not all progeny are exactly identical to the parental cell, due to chance mutations or differences in environment. However, such altered progeny are included when the above terms are used.

B. General Description

The methods illustrated below to obtain DNA sequences encoding ASP are merely for purposes of illustration and are typical of those that might be used. However, other procedures may also be employed, as is understood in the art.

B.1. The Nature of the Surfactant Complex

The alveolar surface of lung has been studied extensively by a number of techniques, and by a number of groups. It appears that the basement membrane of the alveolus is composed of type I and type II alveolar cells, of which the type II cells comprise approximately 3% of the surface. The type II cells are responsible for the exocrine secretion of materials into a lining fluid layer covering the basement membrane, which materials decrease the surface tension between the liquid of the lining and the gas phase of the contained volume. The fluid layer, then, is comprised of water derived from the blood plasma of the alveolar capillaries, and the surfactant secretions of the type II cells.

The type II cells, themselves, contain 60–100 pg of protein and about 1 pg of lipid phosphorus per cell where the ratio between type II cell DPPC and PG phosphorus is about 8 to 1. Studies of the apoprotein components have been based on pulmonary lavage from various species, and have been shown to comprise two major proteins, as discussed above, of approximate molecular weights 10–20 kd and of 32 kd (Kikkawa, Y., et al, *Laboratory Investigation* (1983) 49: 122–139.) It is not clear whether the apoproteins are bound to the phospholipid component (King, R. J.; et al, *Am Rev Respir Dis* (1974) 110: 273) or are not (Shelly, S. A., et al, *J Lipid Res* (1975) 16: 224).

It has been shown that the higher molecular weight protein obtained by pulmonary lavage of dogs, and separated by gel electrophoresis is composed of 3 major components of molecular weight 29,000, 32,000, and 36,000 daltons. (See, U.S. Ser. No. 665,018, filed 26 Oct. 1984, assigned to the same assignee, and incorporated herein by reference.) The 32,000 dalton protein was used to obtain sequence data, as set forth below; however, all 3 of these proteins have identical N-terminal sequences, and there is evidence that they differ only in degree of glycosylation. Digestion of the 36 kd and 32 kd bands with endoglycosidase F, which removes carbohydrate side chains, results in products which co-migrate with the 29 kd component. The mobility of the 29 kd component is unaffected by this treatment. It has also been shown that the 32 kd fraction aggregates into dimers and trimers.

The smaller molecular weight proteins are extracted with more difficulty, but these, too, appear to be mixtures (Phizackerley, et al (supra); description below).

B.2. Cloning of Coding Sequences for Canine and Human ASP Proteins

The entire canine and human ASP 32K protein encoding sequences have been cloned, and are available for expression in a variety of host cells as set forth in ¶ C below. In addition, DNA sequences encoding several of the lower molecular weight proteins from both human and canine sources have also been obtained.

The canine 32K sequence was obtained from a cDNA library prepared from mRNA isolated from adult canine lung, by probing with two sets of synthetic oligonucleotides, one prepared to accomodate all the possible sequences encoding amino acids 1–5 of the N-terminal sequence and the other amino acids 7–11 of that sequence, as well as a single 15-mer encoding the amino acids 1–5, selected on the basis of mammalian codon preference. Immobilized cDNA from the library constructed in E. coli was probed using these oligonucleotide sets. False positives were minimized by requiring hybridization to more than one set. Successfully hybridizing clones were sequenced, and one was shown to contain the correct N-terminal sequence.

The cDNA insert from the successful clone, excised with PstI, was then used as a probe of the original canine cDNA library, to obtain two additional clones containing inserts encoding other regions of the ASP which, together with this probe, span 844 nucleotides containing the complete coding sequence of canine 32K ASP. The entire nucleotide sequence of the three appropriate inserts, and the deduced 256 amino acid sequence are shown in FIG. 1.

This same originally retrieved N-terminal encoding fragment used above was also used as a probe to obtain fragments from a human genomic library in λ phage Charon 28. The entire coding sequence for human ASP 32K protein was found to be contained in a single phage plaque, and to be contained within 2 contiguous BamHI fragments, a 5' 1.2 kb and a 3' 3.5 kb fragment. The pertinent portions of these fragments, encoding human ASP, and containing 3 introns, are shown in FIG. 3; the deduced amino acid sequence of human ASP, contains 228 amino acids, and is preceded by a signal sequence of at least 25 amino acids. The human 32K ASP cDNA corresponding to the full length protein was also obtained by probing human cDNA libraries derived from human fetal and adult lung mRNA.

Extensive homology exists between the canine and human 32K amino acid sequences.

Similar strategies were followed in obtaining cDNA encoding human and canine 10K ASP. The canine lung cDNA library described above was probed with two synthetic oligomer mixtures designed to correspond to the N-terminal amino acid sequence of a 16.5 kd (on unreduced gels) canine protein, and clones hybridizing to both probes were recovered and sequenced. One of these clones, which contained canine ASP encoding sequence, was used to probe a cDNA library prepared in bacteriophage gt10 from mRNA isolated from adult human lung to obtain a human 10K ASP encoding clone.

B.3. Expression of ASP

As the nucleotide sequences encoding the various human and canine ASP are now available, these may be expressed in a variety of systems as set forth in ¶ C. If procaryotic systems are used, an intronless coding sequence should be used, along with suitable control sequences. The cDNA clones for any of the above ASP proteins may be excised with suitable restriction enzymes and ligated into procaryotic vectors for such expression. For procaryotic expression of ASP genomic DNA, the DNA should be modified to remove the introns, either by site-directed mutagenesis, or by retrieving corresponding portions of cDNA and substituting them for the intron-containing genomic sequences. The intronless coding DNA is then ligated into expression vectors for procaryotic expression.

As exemplified below, ASP encoding sequences may also be used directly in an expression system capable of processing the introns, usually a mammalian host cell culture. To effect such expression, the genomic sequences can be ligated downstream from a controllable mammalian promoter which regulates the expression of these sequences in CHO cells.

B.4. Protein Recovery

The ASP protein may be produced either as a mature protein or a fusion protein, or may be produced along with a signal sequence in cells capable of processing this sequence for secretion. It is advantageous to obtain secretion of the protein, as this minimizes the difficulties in purification; thus it is preferred to express the human ASP gene which includes the codons for native signal sequence in cells capable of appropriate processing. It has been shown that cultured mammalian cells are able to cleave and process heterologous mammalian proteins containing signal sequences, and to secrete them into the medium (McCormick, F., et al, *Mol Cell Biol* (1984) 4: 166).

When secreted into the medium, the ASP protein is recovered using standard protein purification techniques. The purification process is simplified, because relatively few proteins are secreted into the medium, and the majority of the secreted protein will, therefore, already be ASP. However, while the procedures are more laborious, it is within the means known in the art to purify this protein from sonicates or lysates of cells in which it is produced intracellularly in fused or mature form.

B.5. Assay for ASP Activity

In vitro methods have been devised to assess the ability of ASP proteins to function by reducing surface tension (synonymous with increasing surface pressure) to generate a film on an aqueous/air interface. Studies using these methods have been performed on the isolated native 10K canine ASP. Benson, B. J., et al *Prog Resp Res* (1984) 18: 83–92; Hagwood, S., et al, *Biochemistry* (1985) 24: 184–190.)

Tanaka, Y, et al, *Chem Pharm Bull* (1983) 31: 4100–4109 disclose that a 35 kd protein obtained from bovine lung enhanced the surface spreading of DPPC; Suzuki, Y., *J Lipid Res* (1982) 23: 62–69; Suzuki, Y., et al, *Prog Resp Res* (1984) 18: 93–100 showed that a 15 kd protein from pig lung enhanced the surface spreading of the lipid-protein complex from the same source.

Since the function of the surfactant complex in vivo is to create a film at the air/aqueous interface in order to reduce surface tension, the ability of ASP proteins to enhance the formation of the film created by the spread of lipid or lipoprotein at such a surface in an in vitro model is clearly relevant to its utility.

B.6. Administration and Use

The purified proteins can be used alone and in combination in pharmaceutical compositions appropriate for administration for the treatment of respiratory distress syndrome in infants or adults. The compositions and protein products of the invention are also useful in treating related respiratory diseases such as pneumonia and bronchitis. For use in such treatment, either of the components, but preferably the 32K component, either alone or, even more preferably, in combination with the 10K component of human ASP is combined with natural or synthetic lipids to reconstruct a surfactant complex. The complex contains about 50% to almost 100% (wt/wt) lipid and 50% to less than 1% ASP; preferably ASP is 5%–20% of the complex. The lipid portion is preferably 80%–90% (wt/wt) DPPC with the remainder unsaturated phosphatidyl choline, phosphatidyl glycerol, triacylglycerols, palmitic acid or mixtures thereof. The complex is reassembled by mixing a solution of ASP with a suspension of lipid lipsomes, or by mixing the lipid protein solutions directly in the presence of detergent or an organic solvent. The detergent or solvent may then be removed by dialysis.

While it is possible to utilize the natural lipid component from lung lavage in reconstructing the complex, and to supplement it with appropriate amounts of ASP proteins, the use of synthetic lipids is clearly preferred. First, there is the matter of adequate supply, which is self-evident. Second, purity of preparation and freedom from contamination by foreign proteins, including infectious proteins, which may reside in the lungs from which the natural lipids are isolated, are assured only in the synthetic preparations. Of course, reconstitution of an effective complex is more difficult when synthetic components are used.

While the 32K human ASP may be used alone as the protein component of the compositions, the combination of 32K and 10K proteins is preferred. The protein ratio is typically in the range of 3:1 to 10:1, preferably 5:1, for 32K:10K group. The 32K protein may be added directly to an aqueous suspension of phospholipid vesicles in an aqueous solution; because it is so hydrophobic, the 10K protein is added to the lipids in an organic solvent, such as chloroform, the solvents evaporated, and the vessicles re-formed by hydration.

The compositions containing the complex are preferably those suitable for endotracheal administration, i.e., generally as a liquid suspension, as a dry powder "dust" or as an aerosol. For direct endotracheal administration, the complex is suspended in a liquid with suitable excipients such as, for example, water, saline, dextrose, or glycerol and the like. The compositions may also contain small amounts of non-toxic auxiliary substances such as pH buffering agents, for example, sodium acetate or phosphate. To prepare the "dust", the complex, optionally admixed as above, is lyophylized, and recovered as a dry powder.

If to be used in aerosol administration, the complex is supplied in finely divided form along with an additional surfactant and propellent. Typical surfactants which may be administered are fatty acids and esters, however, it is preferred, in the present case, to utilize the other components of the surfactant complex, DPPC and PG. Useful propellents are typically gases at ambient conditions, and are condensed under pressure. Lower alkanes and fluorinated alkanes, such as Freon, may be used. The aerosol is packaged in a container equipped with a suitable valve so that the ingredients may be maintained under pressure until released.

The surfactant complex is administered, as appropriate to the dosage form, by endotracheal tube, by aerosol administration, or by nebulization of the suspension or dust into the inspired gas. Amounts of complex between about 0.1 mg and 200 mg, preferably 50-60 mg/kg body weight, are administered in one dose. For use in newly born infants, one administration is generally sufficient. For adults, sufficient reconstituted complex is administered to replace demonstrated levels of deficiency (Hallman, M., et al, *J Clinical Investigation* (1982) 70: 673-682).

C. Standard Methods

Most of the techniques which are used to transform cells, construct vectors, extract messenger RNA, prepared cDNA libraries, and the like are widely practiced in the art, and most practitioners are familiar with the standard resource materials which describe specific conditions and procedures. However, for convenience, the following paragraphs may serve as a guideline.

C.1. Hosts and Control Sequences

Both procaryotic and eucaryotic systems may be used to express the ASP encoding sequences: procaryotic hosts are the most convenient for cloning procedures. Procaryotes most frequently are represented by various strains of *E. coli*; however, other microbial strains may also be used. Plasmid vectors which contain replication sites and control sequences derived from a species compatible with the host are used; for example, *E. coli* is typically transformed using derivatives of pBR322, a plasmid derived from an *E. coli* species by Bolivar, et al, *Gene* (1977) 2: 95. pBR322 contains genes for ampicillin and tetracycline resistance, and thus provides additional markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al, *Nature* (1977) 198: 1056 and the tryptophan (trp) promoter system (Goeddel, et al *Nucleic Acids Res* (1980) 8: 4057 and the lambda derived $P_L$ promoter and N-gene ribosome binding site (Shimatake, et al, *Nature* (1981) 292: 128).

In addition to bacteria, eucaryotic microbes, such as yeast, may also be used as hosts. Laboratory strains of *Saccharomyces cerevisiae*, Baker's yeast, are most used although a number of other strains are commonly available. Vectors employing, for example, the $2\mu$ origin of replication of Broach, J. R., *Meth Enz* (1983) 101: 307, or other yeast compatible origins of replications (see, for example, Stinchcomb, et al, *Nature* (1979) 282: 39, Tschempe, et al, *Gene* (1980) 10: 157 and Clarke, L, et al, *Meth Enz* (1983) 101: 300) may be used. Control sequences for yeast vectors include promoters for the synthesis of glycolytic enzymes (Hess, et al, *J. Adv Enzyme Req* (1968) 7: 149; Holland, et al, *Biochemistry* (1978) 17: 4900). Additional promoters known in the art include the promoter for 3-phosphoglycerate kinase (Hitzeman, et al, *J Biol Chem* (1980) 255: 2073), and those for other glycolytic enzymes. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization. It is also believed terminator sequences are desirable at the 3' end of the conding sequences. Such terminators are found in the 3' untranslated region following the coding sequences in yeast-derived genes.

It is also, of course, possible to express genes encoding polypeptides in eucaryotic host cell cultures derived from multicellular organisms. See, for example, *Tissue Cultures*, Academic Press, Cruz and Patterson, editors (1973). These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) Fiers, et al, *Nature* (1978) 273: 113), or other viral promoters such as those derived from polyoma, Adenovirus 2, bovine papiloma virus, or avian sarcoma viruses. The controllable promoters, hMTII (Karin, M., et al, *Nature* (1982) 299: 797-802) may also be used. General aspects of mammalian cell host system transformations have been described by Axel; U.S. Pat. No. 4,399,216 issued 16 Aug. 1983. It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes.

C.2. Transformations

Depending on the host cell used, transformation is done using standard techniques appropriate to such cells. The calcium treatment employing calcium chloride, as described by Cohen, S. N., *Proc Natl Acad Sci* (*USA*) (1972) 69: 2110, or the $RbCl_2$ method described in Maniatis, et al, *Molecular Cloning: A Laboratory Manual* (1982) Cold Spring Harbor Press, p. 254 may be used for procaryotes or other cells which contain substantial cell wall barriers. For mammalian cells without such cell walls, the calcium phosphate precipitation method of Graham and van der Eb, *Virology* (1978) 52: 546, optionally as modified by Wigler, M., et al, *Cell* (1979) 16: 777-785 may be used. Transformations into yeast may be carried out according to the method of Van Solingen, P., et al, *J Bact* (1977) 130: 946 or of Hsiao, C. L., et al, *Proc Natl Acad Sci* (*USA*) (1979) 76: 3829.

C.3. *Probing cDNA or Genomic Libraries* cDNA or genomic libraries are screened using the colony hybridization procedure. Each microtiter plate is replicated onto duplicate nitrocellulose filter papers (S & S type BA-85) and colonies are allowed to grow at 37° C. for 14-16 hr on L agar containing 15 $\mu$g/ml tetracycline. The colonies are lysed with 10% SDS and the DNA is fixed to the filter by sequential treatment for 5 min with 500 mM NaOH/1.5M NaCl, then 0.5M Tris HCl (pH 8.0)/1.5M NaCl followed by 2×standard saline citrate (SSC). Filters are air dried and baked at 80° C. for 2 hr.

For nick-translated probe, the duplicate filters are prehybridized at 42° C. for 16–18 hr with 10 ml per filter of DNA hybridization buffer (50% formamide (40% formamide if reduced stringency), 5×SSC, pH 7.0, 5×Denhardt's solution (polyvinylpyrrolidine, plus Ficoll and bovine serum albumin; 1× =0.02% of each), 50 mM sodium phosphate buffer at pH 7.0, 0.2% SDS, 50 μg/ml yeast tRNA, and 50 μg/ml denatured and sheared salmon sperm DNA).

Samples are hybridized with nick-translated DNA probes at 42° C. for 12–36 hr for homologous species and 37° C. for heterologous species contained in 5 ml of this same DNA hybridization buffer. The filters are washed two times for 30 min, each time at 50° C., in 0.2×SSC, 0.1% SDS for homologous species hybridization, and at 50° C. in 3×SSC, 0.1% SDS for heterologous species hybridization. Filters are air dried and autoradiographed for 1–3 days at −70° C.

For synthetic (15–30 mer) oligonucleotide probes, the duplicate filters are prehybridized at 42° C. for 2–8 hr with 10 ml per filter of oligo-hybridization buffer (6×SSC, 0.1% SDS, 1 mM EDTA, 5× Denhardt's, 0.05% sodium pyrophosphate and 50 μg/ml denatured and sheared salmon sperm DNA).

The samples are hybridized with kinased oligonucleotide probes of 15–30 nucleotides under conditions which depend on the composition of the oligonucleotide. Typical conditions employ a temperature of 30°–42° C. for 24–36 hr with 5 ml/filter of this same oligo-hybridization buffer containing probe. The filters are washed two times for 15 min at 23° C., each time with 6×SSC, 0.1% SDS and 50 mM sodium phosphate buffer at pH 7, then are washed once for 2 min at the calculated hybridization temperature with 6×SSC and 0.1% SDS, air dried, and are autoradiographed at −70° C. for 2 to 3 days.

C.4. cDNA Library Production

Double-stranded cDNA is synthesized and prepared for insertion into the plasmid vector pBR322 using homopolymeric tailing mediated by calf thymus terminal transferase (Sutcliffe, J. G., *Nucleic Acid Res* (1978) 5: 2721–2732). First strand cDNA is synthesized by the RNA-dependent DNA polymerase from Avian Myeloblastosis Virus, by priming with oligo (dT) 12–18 on 5 μg mRNA. The RNA template is then liberated from the nascent DNA strand by denaturation at 100° C. for 5 min, followed by chilling on ice. Second strand DNA is synthesized by using the large fragment of DNA polymerase I of *E. coli*, relying on self-priming at the 3′-end of the first strand molecule, thereby forming a double-stranded hairpin DNA. These molecules are blunt-ended at the open-ended termini, and the hairpin loop is cleaved open with S1 nuclease from *Aspergillus oryzae*. S1 nuclease digestion of the double-stranded cDNA takes place in 300 mM NaCl, 30 mM NaOAc, pH 4.5, 3 mM ZnCl$_2$ for 30 min at 37° C. with 600 units enzyme. The cDNA is extracted with phenol:chloroform, and small oligonucleotides are removed by three ethanol precipitations in the presence of ammonium acetate. This is done as follows: a half volume of 7.5M ammonium acetate and two volumes ethanol are added to the cDNA solution, which is precipitated at −70° C. The blunt-ended, double-stranded cDNA is then fractionated by size using gel filtration through a column (0.3×14 cm) Sepharose 4B (Pharmacia Fine Chemicals, Piscataway, NJ) or by ultracentrifugation in 5–20% glycerol gradient followed by fractionation of the gradient. cDNA roughly greater than the desired length, e.g., 300 base pairs is retained and recovered by precipitation with 70% ethanol. Short (10–30 nucleotides) polymeric tails of deoxycytosine are added to the 3′ termini of the cDNA using a reaction containing 0.2M potassium cacodylate, 25 mM Tris, pH 6.9, 2 mM dithiothreitol, 0.5 mM CoCl$_2$, 200 mM cDTP, 400 μg/ml BSA, and 40 units calf thymus terminal deoxynucleotide transferase for 5 min at 22° C. The reaction is extracted with phenol:chloroform, and small oligonucleotides are removed with three ethanol precipitations in the presence of ammonium acetate.

The dC-tailed cDNA is annealed with pBR322 which has been cleaved with PstI and tailed with oligo dG: 2.5 μg pBR322-dG DNA is annealed with the cDNA at a vector concentration of 5 μg/ml, and the hybrids are transferred into *E. coli* MC1061 by the CaCl$_2$-treatment described by Casabadan, M., et al, *Mol Biol* (1980) 138: 179–207.

C.5. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme is about 20 μl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65: 499–560.

Restriction cleaved fragments may be blunt ended by treating with the large fragment of E. coli DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 5–10 μM dNTPs. The Klenow fragment fills in at 5′ sticky ends but chews back protruding 3′ single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Synthetic oligonucleotides are prepared by the method of Efimov, V. A., et al (*Nucleic Acids Res* (1982) 6875–6894), and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM MgCl$_2$, 5 mM dithiothreitol, 1-2 mM ATP, 1.7 pmoles γ32P-ATP (2.9 mCi/mmole), 0.1 mM spermidine, 0.1 mM EDTA.

Ligations are performed in 15-50 μl volumes under the following standard conditions and temperatures: 20 mM Tris-Cl pH 7.5, 10 mM MgCl$_2$, 10 mM DTT, 33 μg/ml BSA, 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 μg/ml total DNA concentrations (5-100 nM total end concentration). Intermolecular blunt end ligations (usually employing a 10-30 fold molar excess of linkers) are performed at 1 μM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of Na+ and Mg+2 using about 1 unit of BAP or CIP per μg of vector at 60° for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis is used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered. Details of site specific mutation procedures are described below in specific examples.

C.6. Verification of Construction

In the constructions set forth below, correct ligations for plasmid construction are confirmed by first transforming E. coli strain MC1061 obtained from Dr. M. Casadaban (Casadaban, M., et al. *J Mol Biol* (1980) 138: 179-207) or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci (USA)* (1969) 62: 1159, optionally following chloramphenicol amplification (Clewell, D. B., *J. Bacteriol* (1972) 110: 667). The isolated DNA is analyzed by restriction and/or sequenced by the dideoxy method of Sanger, F., et al, *Proc Natl Acad Sci (USA)* (1977) 74: 5463 as further described by Messing, et al, *Nucleic Acids Res* (1981) 9:309, or by the method of Maxam, et al, *Methods in Enzymology* (1980) 65: 499.

C.7. Hosts Exemplified

Host strains used in cloning and expression herein are as follows:

For cloning and sequencing, and for expression of construction under control of most bacterial promoters, E. coli strain MC1061 was used.

For M13 phage recombinants, E. coli strains susceptible to phage infection, such as E. coli strain JM101 are employed.

The cells used for expression are Chinese hamster ovary (CHO) cells.

D. Cloning and Expression of ASP

Both canine and human ASP proteins were obtained in purified form. Canine cDNA was used to provide probes for the human ASP genomic and cDNA library.

D.1. Purification of Canine ASP

D.1.a. Isolation of the Surfactant Complex

Lung surfactant complex was prepared from canine lungs obtained from exsanguinated canines. All procedures, including the lavage, were performed at 4° C. and the isolated material was stored at −15° C.

The lungs were degassed and lavaged 3 times with one liter per lavage of 5 mM Tris-HCl, 100 mM NaCl, pH 7.4 buffer. The Ca+2 concentration of this buffer was less than 5×10$^{-6}$M (Radiometer F2112 Ca; Radiometer A/S, Copenhagen, Denmark). The pooled lung washings were spun at 150×g$_{av}$ for 15 min (Sorval RC2-B) to remove cellular material. The supernatant was then spun at 20,000×g$_{av}$ for 15 hr (Beckman L3-40) using a type 15 rotor (Beckman Instruments), and the resulting pellet was dispersed in buffer containing 1.64M sodium bromide. After equilibration for 1 hr, the suspension was spun at 100,000×g$_{av}$ for 4 hr (Beckman L5-50B) in a SW28 rotor (Beckman Instruments). The pellicle was resuspended in buffer and spun at 100,000×g$_{av}$ for 1 hr (Beckman L-5-50B). This pellet containing the complex was resuspended in double distilled water.

D.1.b. Extraction of Lipid and 10K Protein

Pellet resuspended in water at a concentration of 10-15 mg phospholipid/ml was injected into a 50-fold volume excess of n-butanol (Sigrist, H., et al, *Biochem Biophys Res Commun* (1977) 74: 178-184) and was stirred at room temperature for 1 hr. After centrifugation at 10,000×g$_{av}$ for 20 min (Sorval RC2-B), the pellet, which contains the 32K ASP is recovered for further purification as described below. The supernatant, which is a single phase, contains the lipids and the lower molecular weight proteins. To obtain the lipids, the supernatant was dried under vacuum at 40° C. and the lipids were extracted (Folch, J., et al, *J. Biol Chem* (1957) 226: 497-509).

To obtain the hydrophobic protein, the supernatant was subjected to rotovap to remove the butanol, and further dried by addition of ethanol followed by rotovap. The dried residue was suspended in redistilled chloroform containing 0.1N HCl, and insoluble material removed by centrifugation.

The resulting solution was chromatographed over an LH-20 column (Pharmacia) and developed in chloroform. (LH-20 is the hydroxypropyl derivative of Sephadex G-50; it is a hydrophobic gel which is inert to organic solvents.) The proteins are excluded; lipids/phospholipids elute from the included volume.

Protein is recovered from the void volume fractions by evaporation of the chloroform under nitrogen, and then subjected to sizing on polyacrylamide gels. When run under non-reducing conditions, three bands of 16.5 kd, 12 kd, and 10 kd were obtained; under reducing conditions, a single broad band of 10-12 kd was found.

The 16.5 kd and 12 kd bands from the non-reduced gels were subjected to N-terminal analysis by Edman degradation, to give the following sequences:

For 16.5 kd: ?-Pro-Ile-Pro-Leu-Pro-Tyr-Cys-Trp-Leu-Cys-Arg-Thr-Leu-Ile-Lys-Arg-Ile-Gle-Ala-Met-Ile-Pro-Lys-Gly-Val-Leu-Ala-Val-Thr-?-Gly-Gln-

For 12 kd: Ile-Pro-Cys-Phe-Pro-Ser-Ser-Leu-Lys-Arg-Leu-Leu-Ile-Ile-Val-Trp

D.1.c. Protein Fractionation and Verification as ASP 32K Protein

The precipitate from the n-butanol extraction above was dried under nitrogen and washed twice in 20 ml of buffer containing 20 mM octyl-$\beta$-D-glucopyranoside. After centrifugation at $100,000 \times g_{av}$ for 1 hr (Beckman L5-50B), the pellet was dispersed in 0.3M lithium diiodosalicylate, 0.05M, pyridine (pH 8.4) on ice, diluted with an equal volume of water, and mixed with a volume of n-butanol equal to the aqueous phase. A total of 9 n-butanol-water partitions were performed to lower the detergent concentration in the aqueous phase. The final lower, aqueous phase containing the protein was lyophilized for 15 hr. taken up in 2 ml of buffer and spun at $100,000 \times g_{av}$ (Beckman L5-50B) to remove any remaining insoluble material. The lithium diiodosalicylate concentration in the final sample, calculated from an extinction coefficient of $4 \times 10^3$ at 323 nm (Marchesi, V. T. and Andrews, E. P., *Science* (1971) 174: 1247-1248), was less than 10 $\mu$M.

The thus purified canine ASP 32K apoprotein was reconstituted with surfactant lipids purified as above. The reconstituted material had surface activity as measured by the surface balance and its in vivo biological activity was demonstrated by inspiration into fetal rabbits maintained on a ventilator.

D.1d. Further Protein Purification

The protein fraction obtained in the previous subparagraph was reduced by incubation with 50 mM DTT in 1% SDS, 50 mM Tris-HCl, 1 mM EDTA pH 7.5 at 37° C. for 1 hr, aklylated with 100 mM iodoacetamide (Sigma) at 0° C. for 30 min, and subjected to polyacrylamide gel eletrophoresis by the procedure of Laemmli, U. K., *Nature* (1970) 227: 680-685. The proteins were visualized by soaking the gel in 4M sodium acetate solution and the 32K band was sliced out with a razor blade, and electroluted by the protocol of Hunkapiller, M. W., et al, *Methods in Enzymology* (1983) 91: 227-235, New York, Academic Press, using the CBS Scientific (Del Mar, Calif.) electrolution device.

The eluted protein was lyophilized and its N-terminal amino acid sequence was determined from one nanomole of protein using the Applied Biosystems 470A gas-phase sequencer (Applied Biosystems Inc., Foster City, CA) in accordance with the instructions of the manufacturer. PTH amino acids were identified with a Beckman 334T HPLC, using a 0.46×25 cm IBM CN-column. The gradient applied was as indicated in Hunkapiller, N. W., and Hood, L. E., *Methods in Enzymology* (1983) 91: 486-492, New York, Academic Press, with the following modifications: Instead of a binary gradient system a ternary gradient system was used in which acetonitrile and methanol were pumped by separate pumps and the ratio of the two varied with time over the course of the gradient, with appropriate modification of the gradient program; instead of the Permaphase ETH$^r$ guard column, a "5×0.46 cm IBM CN" analytical "mini-column", was used; and the column was heated to 28° C., rather than to 32° C.

The N-terminal amino acid sequence was:

```
1                   5                    10
Ile—Glu—Asn—Asn—Thr—Lys—Asp—Val—Cys—Val—

15                   20
—Gly—Asn—Hyp—Gly—Ile—Hyp—Gly—Thr—Hyp—Gly—

25                   30
—Ser—His—Gly—Leu—Hyp—Gly—Arg—?-Gly—Arg—?-

Gly—Val.
```

"Hyp" indicates the modified amino acid hydroxyproline.

Amino acid composition data for the canine 32K protein show a hydroxyproline content consistent with the hydroxylation of proline residues in the deduced sequence (see below) which appear in the collagen-like pattern Gly-X-Hyp. As this pattern is also shown in the human N-terminal sequence it is probable, by analogy to the canine data, that similarly disposed prolines in the human sequence are hydroxylated.

Information regarding processing was obtained by purification and sequencing of collagenase treated canine ASP.

Purified canine ASP was digested with bacterial collagenase (Worthington, Freehold NJ) at a 1:1 enzyme:-substrate ratio in 5 mM Tris pH 7.4-5 mM Cacl$_2$ at 37° C. That produced a 22 kd limit digest product as analyzed on SDS gels. This 22 kd band was electroeluted from a gel and subjected to amino acid sequence analysis as described above. Two amino acids were identified at each cycle, indicating the the collagenase treatment had produced two peptides which remain linked by a disulfide-bridge. From the cDNA clone sequence it can be demonstrated that the two sequences correspond to amino acids 78-110 and 203-231 in the intact molecule. The sequences obtained are:

```
  2        4        6        8       10
Gly—Pro—Hyp—Gly—Leu—Pro—Ala—Ser—Leu—Asp—
Gly—Lys—Glu—Gln—Cys—Val—Glu—Met—Tyr—Thr—
  12       14       16       18       20
—Glu—Glu—Leu—Gln—Thr—Thr—Leu—His—Asp—Leu—
—Asp—Gly—Gln—Trp—Asn—Asn—Lys—Asn—Cys—Leu—
```

-continued

```
       22      24      26      28      30
—Arg—His—Gln—Ile—Leu—Gln—Thr—Met—Gly—Val—
—Gln—Tyr—Arg—Leu—Ala—Ile—Cys—Glu—Phe
                    32
              —Leu—Ser—Leu
``` and demonstrate that translation is complete, and that the C-terminus of the protein is intact.

D.1e. Isolation of Human ASP

Human 32K and lower molecular weight ASP was prepared following the procedure described above for canine proteins from a patient suffering from alveolar proteinosis (a syndrome which results from the presence of excess surfactant in the lung).

The 32K ASP has the N-terminal sequence:

```
1               5               10
Glu—Val—Lys—Asp—Val—Cys—Val—Gly—Ser—Hyp—
                    15
            —Gly—Ile—Hyp—Gly—Thr—Hyp—Gly
```

Amino acids 3-17 of the human sequence are precisely homologous to amino acids 6-20 of the canine 32K protein except for the serine at position 9.

The isolated low molecular weight hydrophobic proteins show bands corresponding to 16.5 kd, 14 kd and 10 kd when subjected to polyacrylamide gel electrophoresis under non-reducing conditions. Under reducing conditions, a single broad band corresponding to 10-11 kd is obtained.

D.2. Isolation of Canine Lung mRNA

Total RNA was isolated from an adult canine lung by the method of Chirgwin, J. M., et al, *Biochemistry* (1979) 18: 5294-5299. The lung tissue was first pulverized by grinding with a mortar and pestle in liquid N$_2$, and homogenized in a solution of 6M guanidine thiocyanate, 0.05M Tris-HCl, pH 7.0, 0.1M-β-mercaptoethanol, 0.5% Sarcrosyl. This homogenate was made 2.0M in CsCl and layered over a 5.7M CsCl cushion in 0.01M ethylenediaminetetraacetic acid (EDTA) and 0.05M Tris-HCl, pH 9.0. The RNA was pelleted through this cushion by centrifugation at 115,000×g for 16 hr, thereby separating it from the cellular DNA and protein which do not sediment through the higher density CsCl solution. The RNA was then dissolved in 0.01M Tris-HCl, pH 7.4, 0.005M EDTA, 1.0% sodium dodecylsulfate (SDS), extracted with a 1:1 mixture of chloroform and phenol, and precipitated from 70% ethanol. The polyadenylated RNA (poly A+ RNA) fraction was obtained by affinity chromatography through oligo (dT) cellulose as described by Aviv, H., and Leder, P., *Proc Natl Acad Sci* (USA) (1972) 69: 1840-1412.

D.3. Construction and Screening of Canine Lung cDNA Library

Adult canine lung poly A+ RNA prepared as in ¶ D.2 was used to construct a cDNA library as described in ¶ C.4, 5 µg mRNA yielded about 25 ng of cDNA, size-selected to greater than 300 base pairs. The library contained about 200,000 independent recombinants. Of these, 40,000 recombinants were plated on nitrocellulose filters. These filters served as the masters for subsequent replicas (in accordance with the method of Hanahan, D., and Meselson, M., *Gene* (1980) 10: 63-75.

cDNA Encoding the 32K Protein

Three probes were constructed: a mixture of 24×14-mer sequences complementary to the amino acids 1-5 having the sequence

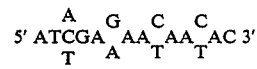

(probe a); 64×14-mers complementary to the amino acids 7-11 having the sequence

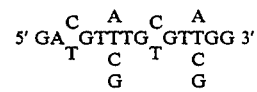

(probe b); and a single 15-mer

selected on the basis of mammalian codon preference (probe c). Each oligonucleotide mixture and the single unique oligonucleotide were synthesized on a Biosearch SAM I oligonucleotide synthesizer (Biosearch, Inc., San Rafael, CA), by a modification of the standard phosphotriester method using metsitylenesulfonyl chloride in the presence of N-methylimidazole as condensing reagents as described by Efimov, V. A., et al, *Nucleic Acids Res* (1982) 10: 6875-6894, and purified by polyacrylamide gel electrophoresis.

For hybridization, xix replica filters were prepared from each master filter, so that each colony could be screened in duplicate with each of three oligonucleotide probes. Colonies recovered after replication off the master filters were placed on agar plates containing 170 µg/ml chloramphenicol for 18 hr. The colonies were then prepared for hybridization according to the method of Grunstein, M., and Hogness, D., *Proc Natl Acad Sci* (1975) 72: 3961-3972.

The filters were baked for 2 hr at 80° C. under vacuum and then washed for 4 hr at 68° C. with shaking in a large volume of 3X SSC (where 1X SSC is 0.15M NaCl, 0.015M sodium citrate, pH 7.5), 0.1% SDS. The filters were prehybridized in 6×SSC, 0.1% SDS, 1 mM EDTA, 5×Denhardt's solution (0.1% Ficoll, 0.1% polyvinylpyrrolidone, 0.1% bovine serum albumin) 0.05% sodium pyrophosphate and 50 µg/ml denatured salmon sperm DNA at 42° C. for a minimum of 2 hr.

Duplicate filters were then hybridized with 5×10$^6$ cpm of one of each $^{32}$P-labeled oligonucleotide probe (phosphoryltated in accordance with Maniatis, T., et al, *Molecular Cloning*, (1982) Cold Spring Harbor Laboratories, pp. 122-123) per filter in 10 ml hybridization solution containing identical ingredients as the prehybridization solution. Filters with oligonucleotide probes a, b, and c were hybridized at 37° C., 45° C., and 41° C., respectively. After 1 hr, the thermostat was lowered to 28° C. for probe a and 37° C. for probe b, after which the bath was allowed to equilibrate. Filters with probe c were not hybridized at a lower temperature. The filters were washed twice in 6×SSC, 0.1% SDS at room temperature for 15 min, then washed in 6×SSC, 0.1% SDS at 37° C., 45° C., and 41° C. for probes a, b, and c, respectively, for 2 min. The final washing temperature was obtained form the empirical formula of Suggs, S. V., et al, *Developmental Biology Using Purified*

Genes (ed. D. D. Brown and C. F. Fox), Academic Press, NY, pp. 683–693; that is, $T_d=4(G+C)+2(A+T)$. The hybridized filters were then dried and autoradiographed on Kodaká XAR film with Dupontá Cronex intensifying screens until complete exposures were obtained.

A colony was considered positive if it hybridized in duplicate with all three oligonucleotide probes or with both probes a and b. Of several potential positive clones, one hybridized much more intensely with probes a and b as compared to the others. Sequencing of this clone demonstrated that it encoded a portion of the sequence of canine 32K ASP. It was designated DS-1 and used to obtain the entire 32K canine ASP.

The purified DNA insert of 375 base pairs was excised from pDS-1 by restriction with PstI and prepared using small miniprep methods (Maniatis, et al, supra at p. 366) and was isolated on agarose gels. The intact DNA insert was then subcloned into bacteriophage M13 (Messing, J., and Vieira, J., Gene (1982). 19: 259–268) and sequenced using the dideoxy method of Sanger, F., et al, *Proc Natl Acad Sci* (USA) (1977) 74: 5463–5469. The sequence encoded the N-terminal portion of the approximately 300 amino acid protein, i.e., the 32 residue N-terminal amino acid sequence determined from the purified canine ASP of ¶D.1, and 101 additional downstream amino acids. It also contained 50 base pairs of the 5' untranslated region.

The mRNA pool was assessed to determine the presence of sequences of sufficient length to encode the entire canine ASP sequence by Northern blot. Poly A+ RNA of ¶D.2 was subjected to Northern blot using nick translated DS-1 insert DNA after fractionation by electrophoresis on a 1.4% agarose gel containing methylmercuric hydroxide by the method of Bailey, J. M. and Davidson, N., *Anal Biochem* (1976) 70: 75–85. mRNA hybridizing to probe was 1800–2000 nucleotides in length, clearly larger than the approximately 700 nucleotides needed for the coding sequence.

The DS-1 insert probe was therefore used to rescreen one duplicate set of original filters, which had been treated at 100° C. for 10 min to remove residual oligonucleotide probe. Filters were prehybridized in 0.75M NaCl, 0.075M Na citrate, 50% formamide, 0.5% SDS, 0.02% bovine serum albumin, 0.02% Ficoll-400,000, 0.02% polyvinyl pyrollidone, 0.1% sodium pyrophosphate, 50 µg.ml yeast tRNA and 50 µg/ml denatured sheared salmon sperm DNA) at 42° C. for 18 hr. $5 \times 10^5$ cpm of $^{32}$P-labeled boiled DS-1 cDNA was added per ml fresh hybridization buffer and the filters were incubated in this buffer at 42° C. for 16 hr. They were then washed in 0.03M NaCl and 0.003M sodium citrate and 0.1% SDS two times each for 30 min at 50° C., and exposed for autoradiography overnight. Two additional clones, DS-4 and DS-31, were identified, which, together with DS-1, comprise roughly 1700 base pairs (FIG. 1).

DS-4 and DS-31 were also excised using PstI, subcloned into the PstI site of M13mp9, and sequenced by dideoxy sequencing according to the procedure of Sanger, F. (supra). The entire sequence contains two internal PstI sites. Confirmation of correct sequencing was obtained by dideoxy sequencing of fragments obtained from deduced internal restriction sites, as shown in FIG. 1. The entire nucleotide sequence including the amino acid sequence of ASP deduced from the 256 codon open reading frame is shown in FIG. 1.

cDNA Encoding Canine 10K ASP

Two oligomeric probes were synthesized corresponding to the N-terminal sequence of the 16.5 kd protein using mammalian codon preference tables for codon choice. Probe 1198 was a 36-mer of the sequence 5'-GGTCACAGCCAGGCCCTTGGGGAT-CATGGCCTGGAT-3'; probe 1199 was a 45-mer of the sequence 5'-CTTGATCAGGGTTCT-GCACAGCCAGCAGTAGGGCAGGG-GGATGGG-3'. Both were labelled with $^{32}$P by kinasing.

For hybridization, filters were baked at 80° C. for two hours under vacuum and then washed for 4 hr at 68° C. with shaking in a large volume of 3×SSC containing 0.1% SDS. The filters were prehybridized for several hours at 42° C. in 6×SSc, 5×Denhardt's, 20% formamide, 0.1% SDS, and 100 µg/ml sheared, denatured salmon sperm DNA. Duplicate filters were hybridized in the above buffer containing either 13 ng/ml probe 1198 or 16 ng/ml probe 1199 at an intial temperature of 68° C., and then at 42° C. overnight. The filters were washed twice for 15 min at room temperature in 6×SSC, 0.1% SDS, 0.05% sodium pyrophosphate, then for 5 min at 65° C. in the same buffer, and then dried and autoradiographed.

Of 40,000 clones screened, 8 hybridized to both probes, and were subjected to restriction analysis. Two overlapping clones which when combined span 1520 nucleotides were sequenced, with the results shown in FIG. 2. The arrow indicates the beginning of the mature 16.5 kd protein.

D.4. Isolation of the human 32K ASP Gene

A human genomic library cloned into bacteriophage Charon 28 (Rimm, D. L., et al, *Gene* (1980) 12: 301–310) was obtained from Dr. T. Maniatis, Harvard University. Approximately $1.5 \times 10^6$ phage were grown on E. coli K803, and plaque lysates were transferred to nitrocellulose filters as described by Benton, W. D., et al, *Science* (1977) 196: 180–182. The filters were probed with DS-1 cDNA which had been kinased by the nick-translation method of Rigby, P. W. J., et al, *J Mol Biol* (1977) 113: 237–251. Filters were prewashed in hybridization buffer (0.75M NaCl, 0.75M sodium nitrate, 40% formamide, 0.05% SDS, 0.02% bovine serum albumin, 0.02% Ficoll-400,000, 0.02% polyvinyl pyrollidone, 0.1% sodium pyrophosphate, 50 µg/ml yeast tRNA, 50 µg/ml denatured sheared salmon sperm DNA) at 42° C. for 1 hr. $5 \times 10^5$ cpm probe was added per ml fresh hybridization buffer and the filters were incubated in this buffer at 37° C. for 16 hr. They were then washed in 0.45M NaCl and 0.045M sodium citrate and 0.1% SDS two times at 50° C., and exposed for autoradiography overnight. Six potential clones containing sequences hybridizing to DS-1 cDNA were purified. The most strongly hybridizing clone, gHS-15, was characterized.

A 700 bp EcoRI fragment from gHS-15 hybridized with the DS-1 probe and was chosen for sequence analysis. This EcoRI fragment was purified, inserted into M13mp9, sequenced and found to be extensively homologous with the corresponding canine sequence.

The entire human coding region was contained within two contiguous BamHI fragments: a 5' 1.2 kb and a 3' 3.5 kb fragment. Both BamHI fragments were individually subcloned into the BamHI site of M13mp8 and sequenced. Additional fragments were similarly sequenced according to the strategy shown in FIG. 3.

The sequence information was analyzed using various Intelligenetics (Palo Alto, CA) computer programs in accordance with the instructions of the manufacturer. The regions containing the signal peptide, precursor sequence and mature apoprotein were identified by comparison to the canine ASP cDNA. From the sequence analysis, the 5' terminus of the gene is encoded within the 1.2 kb BamHI fragment and the 3' terminus within the 3.5 kb BamHI fragment. The gene is interrupted by three introns at positions 1218 bp, 1651 bp and 2482 bp, with position 1 being the first bp of the 1.2 kb BamHI fragment. The entire sequence, including the amino acid sequence of human ASP protein deduced is shown in FIG. 3.

D.5. Expression of Human 32K ASP

The phage isolate gHS-15 identified in D.5 as harboring an insert of approximately 16 kb containing the entire human ASP gene was transferred into CHO cells which had been grown in McCoy's 5A medium with 10% fetal bovine serum by co-transformation with pSV2:NEO (Southern, P., et al, *J. Mol Appl Genet* (1982) 1: 327–341), a plasmid containing a functional gene conferring resistance to the neomycin analog G148, which is toxic to mammalian cells. In the transformation, 15 μg of the λ:gHS-15 and 2 μg of pSV2:NEO were applied to a 100 mm dish of CHO cells in a calcium phosphate/DNA coprecipitate according to the method of Wigler, M., et al, Cell (1979) 16: 777–785, with inclusion of a 2 min "shock" with 15% glycerol 4 hr after exposure to the DNA. The cells were transferred to medium containing 1 μg/ml G418, and yielded about 50 stable transformants per 100 mm dish.

Stable transformants were cultured prior to labeling in media supplemented with 0.25 mM ascorbic acid. Two pools of stable transformants and one pool of untreated CHO cells were grown for 1 hr in medium containing 1/10 of normal methionine concentration and then labeled with $^{35}$S-methionine for 8–16 hours, and the $^{35}$S-met labeled total secreted proteins were analyzed by SDS-polyacrylamide gel electrophoresis. The results are shown in FIG. 4. Lane 1 shows the normal CHO secreted proteins. Lanes 2 and 3 display λ:gHS-15 secreted proteins: both of which have an additional 30–36 kd protein corresponding to an expressed ASP protein. To further document the identity of the 30–36 kd protein one can immunoprecipitate the total secreted protein samples with canine ASP antibodies. The vector λ:gHS-15 was deposited with the American Type Culture Collection on 7 December 1984 and has accession no. ATCC 40146.

D.6. Preparation of a Human cDNA Clones for the 32K and 10K Proteins

Human 32K ASP

Human lung was obtained from two fetuses, one 22 weeks, the other 24 weeks of age. 7 g of lung tissue was first pulverized by grinding with a mortar and pestle in liquid $N_2$, and total poly A+ RNA prepared as set forth in ¶D.2 (supra).

A cDNA library was prepared from the mRNA as set forth in ¶C.4. Five μg of lung poly A+ RNA yielded about 25 ng of cDNA, size-selected to greater than 500 base pairs, and gave a library of 300,000 independent recombinants.

60,000 members of the human cDNA library were screened with the canine DS-1 cDNA in the manner described above for the screening of the genomic library. The recombinant colonies were plated on nitrocellulose filters which served as masters for two sets of replicas. The colony filters were then prepared for hybridization according to the method of Grunstein, M., and Hogness, D. (supra). The filters were baked for 2 hr at 80° C. under vacuum and then washed for 4 hr at 68° C. with shaking in a large volume of 3X SSC and 0.1% SDS. Next the filters were prehybridized in 0.75M NaCl, 0.075M sodium nitrate, 40% formamide, 0.5% SDS, 0.02% bovine serum albumin, 0.02% Ficoll-400,000, 0.02% polyvinyl pyrollidone, 50 μg/ml yeast tRNA, 50 μg/ml denatured sheared salmon sperm DNA) at 37° C. for 18 hr. One×10$^6$ cpm of $^{32}$P-labeled DS-1 probe was added per ml of fresh hybridization buffer then incubated for 16 hr at 37° C. The filters were then washed in 0.45M NaCl and 0.045M sodium citrate and 0.01% SDS two times each for 30 min at 50° C., and exposed for autoradiography overnight.

One positively hybridizing clone, HS-6, was further analyzed by sequence determination; HS-6 harbors a 1.2 kb insert which can be released from the vector using PstI digestion, and which bears an internal EcoRI site. Both PstI-EcoRI fragments from the insert were subcloned into the PstI-EcoRI site of M13mp8 and mp9, and partial sequences obtained. The over 200 bp sequenced portion corresponds perfectly to the 3' end of gHS-15. The nucleotide sequence of HS-6 is shown in FIG. 5.

As the HS-6 cDNA insert contained only the 3'-terminal region of the ASP mRNA, the remaining clones were screened for adjacent surfactant sequences using HS-6 as probe. No clones were found in the remainder of the library.

To obtain the complete cDNA encoding human 32K ASP, a randomly primed cDNA was prepared from adult human lung and cloned in the bacteriophage vector gt10 using EcoRI linkers by the procedure of Huynh, T., et al, *cDNA Cloning Techniques: A Practical Approach* (Glover, D., ed) IRL, Oxford. Adult lung is greatly enriched in ASP transcripts as compared to fetal lung tissue (our observations) and therefore affords a greater frequency of obtaining a complete ASP cDNA.

Phage plaques were screened with a $^{32}$P labelled insert from pHS-6 using 5×10$^{-5}$ cpm/ml in 50% formamide, 5×SSC, 0.05% SDS, 5×Denhardt's, tRNA and salmon sperm DNA at 42° C. for 16 hr. The filters were washed twice at 50° C. for 30 min each in 0.2×SSC, 0.1% SDS, dried and autoradiographed.

Two positively hybridizing clones, designated pHS-2 and pHS-5 were isolated. Each contained the entire 32K ASP encoding sequence and most of the 5' untranslated region. Each overlapped with HS-6, which contained most of the 3' untranslated region; the 3' terminus of each clone corresponds to the EcoRI site within the coding region.

Human 10K ASP

The same cDNA library in lambda gt10 was screened on nitrocellulose filters as above using 1×10$^6$ cpm of the canine clone pD10k-1 described above in 40% formamide, 5×SSC, 0.05% SDS, 5×Denhardt's, 50 μg/ml yeast tRNA and 50 μg/ml salmon sperm DNA for 16 hr at 37° C. The filters were washed twice at 50° C. for 30 min in 2×SSC, 0.1% SDS, dried and autoradiographed. Of 40,000 plaques, two were positive, and one, designated lambda H10k-1 containing a 1.5 kb insert was chosen for sequencing. The complete nucleotide and deduced amino acid sequence for the 10 K protein and its precursor are shown in FIG. 6. The mature 10 K protein begins, as shown in the Figure, at nucleotide 614.

D.7. Construction of Expression Vectors

Vectors suitable for expression of the genomic human 32K ASP encoding sequence in mammalian cells, which are capable of processing intron-containing DNA were constructed. Expression is controlled by the metallothionein I (hMTII) control sequences, as described by Karin, M., et al, *Nature* (1982) 299: 797-802.

The host vector, pMT is obtained by ligating the promoter into pUC8 as follows:

Plasmid 84H (Karin, M., et al (supra)) which carries the hMTII gene was digested to completion with BamHI, treated with exonuclease Bal-31 to remove terminal nucleotides, and then digested with HindIII to liberate an 840 bp fragment containing nucleotides −765 to +70 of the hMTII gene (nucleotide +1 is the first nucleotide transcribed). The 840 bp fragment was isolated and ligated with HindIII/HindcII digested pUC8 (Vieira, J., et al, *Gene* (1982) 19: 259-268) and the ligation mixture transformed into *E. coli* MC1061. The correct construction of pMT was confirmed by dideoxy nucleotide sequencing.

In addition, a derivative of the pMT, pMT-Apo, containing C-terminal regulatory signals was also prepared. pMT-Apo harbors a portion of the human liver protein ApoA$_1$ gene (Shoulders, C. C., et al, *Nucleic Acids Res* (1983) 11: 2827-2837) which contains the 3'-terminal regulatory signals. A PstI/PstI 2.2 kb fragment of ApoA$_1$ gene (blunt ended) was cloned into the SmaI site of the pMT polylinker region, and the majority of the ApoA$_1$ gene removed by digestion with BamHI, blunt ending with Klenow, digestion with StuI, and religation. The resulting vector contains roughly 500bp of the ApoA$_1$ gene from the 3' terminus as confirmed by dideoxy-sequence analysis.

Five constructs of the human ASP gene and the pMT and pMT-Apo expression vectors were prepared using the 1.2 kb and 3.5 kb BamHI fragments of gHS-15. All constructs were isolated and confirmed by both restriction analysis and dideoxy sequencing. These constructs were prepared as follows:

1. the 1.2 kb and 3.5 kb BamHI fragments were cloned into the BamHI site of pMT to give pMT:gHS;
2. the 1.2 kb BamHI fragment was truncated at the 5' terminus by digestion with HinfI (position 950) and filled in with Klenow. The truncated fragment was cloned, along with the 3.5 kb fragment into the BamHI site of pMT to give pMT:gHS (HinfI);
3. the fragments of ¶2 were cloned instead into the BamHI site of pMT-Apo to give pMT-Apo:gHS(HinfI);
4. the 3.5 kb BamHI fragment was truncated at the 3' terminus by digestion with EcoRI (position 3434) and filled in with Klenow. This truncated fragment was cloned, along with the truncated 1.2 kb fragment truncated with HinfI as above into the BamHI site of pMT-Apo to give pMT-Apo:gHS(HinfI/EcoRI);
5. the 1.2 kb fragment was truncated at the BstEII site at position 356 and the 3.5 kb fragment at the BstEII site at position 4024. These fragments were cloned into the BamHI site of pMT-Apo to give pMT-Apo:gHS(BstEII).

The resulting pMT:gHS constructs were transferred into CHO cells as set forth in ¶ D.6 except that 10$^{-4}$M ZnCl$_2$ was added with $^{35}$S-methionine to induce the metallothionein promoter and label the proteins produced.

After 8-16 hr the medium is analyzed for $^{35}$S-met labeled total secreted protein which immunoprecipitates with antibodies to canine ASP. Non-immune IgG are used as a control.

D.8. Optimization of Expression

Conditions of expression were optimized, and additional expression vectors containing the SV40 viral enhancer were used to increase the levels of expression in CHO cells. Three vectors were used: pMT:Apo:gHS(HinfI/EcoRI) described above and further characterized below, and pASPc-SV(10) and pASPcg-SV(10) which are constructed as described below.

Enhancer-containing Vectors

To obtain host expression vectors containing the SV40 enhancer in operable linkage to the MT-II promoter an 1100 bp SV40 DNA fragment was inserted into the HindIII site preceding the MT-II promoter sequences in pMT. The SV40 DNA fragment spans the SV40 origin of replication and includes nucleotide 5171 through nucleotide 5243 (at the origin), the duplicated 72 bp repeat from nucleotide 107-250, and continues through nucleotide 1046 on the side of the origin containing the 5' end of late viral mRNAs. This HindIII 1100 bp fragment is obtained from a HindIII digest of SV40 DNA (Buchman, A. R., et al, *DNA Tumor Viruses*, 2d ed (J. Tooze, ed.). Cold Spring Harbor Laboratory, New York (1981), pp. 799-841), and cloned into pBR322 for amplification. The cloning vector was cut with HindIII, and the 1100 bp SV40 DNA fragment isolated by gel electrophoresis and ligated into HindIII-digested, CIP-treated, pMT. The resulting vectors, designated pMT-SV(9) and pMT-SV(10), contain the fragment in opposite orientations preceding the MT-II promoter. In pMT-SV(9), the enhancer is about 1600 bp from the 5' mRNA start site; in the opposite orientation it is approximately 980 bp from the 5' mRNA start site. Both orientations are operable, but the orientation wherein the enhancer sequences are proximal to the start site provides higher levels of expression.

pASPc-SV(10)

The coding sequences for ASP were inserted into the above-described modified form of the host vector pMT-SV(10). First, the 500 bp apoAI fragment was inserted into pMt-SV(10) by isolating this fragment, obtained by digestion of pMT-Apo (described above) and ligating the isolate into EcoRI/BamHI digested pMT-SV(10). The modified vector was digested with BamHI, blunted, and ligated to the cDNA sequences obtained from pHS-5 (White, R. T., et al, *Nature* (1985) 317: 361-363) as a blunted EcoRI digest. The cDNA fragment extends from the EcoRI linker joined to the 5' untranslated region to the naturally occurring EcoRI site in the 3' untranslated region (900 bp). The relevant nucleotide sequences are shown in FIG. 7, where the starred amino acids represent differences in the primary amino acid sequence from that of the protein obtained from pMT-Apo:gHS(HinfI/EcoRI). (The differences result from base changes between human cDNA and the genomic sequences). Initiation of translation is at nucleotide 56, as in the native sequence.

pASPcg-SV(10)

An additional modification was prepared by integrating pASPc-SV(10) and pMT-Apo:gHS(NinfI/EcoRI) sequences. Plasmid pASPc-SV(10) was digested with BamHI and EcoRI, and the isolated larger fragment ligated to the 3' portion of the ASP gene obtained by BamHI/EcoRI(partial) digestion of pMT-Apo:gHS(-HinfI/EcoRI). This represents the portion of the human ASP gene beginning at nucleotide 1154 and extending to nucleotide 3432, this being ligated to the ApoAI gene fragment as above. This construct results in a protein identical to that obtained from pMT-Apo:gHS(HinfI/EcoRI), but different at amino acid positions 25, 30, and 34 from that obtained from pASPc-SV(10). The nucleotide sequence of the relevant insert is shown in FIG. 8.

pMT-Apo:gHS(HinfI/EcoRI)

For the genomic DNA-containing vector, pMT-Apo:gHS(HinfI/EcoRI), the coding sequences were obtained as an HinfI/EcoRI fragment of the gene extending from nucleotide 950 to nucleotide 3432, containing exons 2, 3, and 4, and part of exon 5. See also, White, R. T., et al, *Nature* (1985) 317: 361-363. This fragment was ligated to a 500 bp fragment from the 3' end of the human ApoAI gene (Shoulders, C. C., *Nucleic Acids Res* (1983) 11: 2827-2837) which contains the polyadenylation signal and polyadenylation site as set forth above. The entire ASP-encoding genomic insert is shown ligated to the MT-II promoter in FIG. 9.

It was expected that this vector would produce a protein 23 amino acids longer than the native preprotein (which includes the signal sequence). The construct lacks exon 1 and therefore translation probably initiates at the ATG beginning at nucleotide 987 of the genomic sequence complementary to native preprotein mRNA, which nucleotide normally resides in the first intron. In the production of native preprotein, exon 1 is spliced to exon 2 at nucleotide 1022, deleting this start codon, and permitting translation to initiate at nucleotide 1046. However, the additional residues do not appear to interfere with secretion, and the normal mature protein is secreted from cells expressing this modified form of the gene.

Transformation Procedure

Each of the vectors described above was transformed into CHO cells as follows: Chinese hamster ovary (CHO)-K1 cells were grown on medium composed of a 1:1 mixture of Coon's F12 medium and DME21 medium with 10% fetal calf serum. The competent cells were co-transformed with the vector of interest and pSV2:NEO (Southern, P., et al, *J Mol Appl Genet* (1982) 1: 327-341). pSV2:NEO contains a functional gene conferring resistance to the neomycin analog G418. In a typical transformation, 0.5 μg of pSV2-NEO and 5 μg or more of the expression vector DNA are applied to a 100 mm dish of cells. The calcium phosphate-DNA co-precipitation according to the protocol of Wigler, M., et al, *Cell* (1979) 16: 777-785, was used with the inclusion of a two minute "shock" with 15% glycerol in PBS after four hours of exposure of the DNA.

Briefly, the cells are seeded at 1/10 confluence, grown overnight, washed 2× with PBS, and placed in 0.5 ml Hepes-buffered saline containing the Ca-PO$_4$.DNA co-precipitate for 15 min and then fed with 10 ml medium. The medium is removed by aspiration and replaced with 15% glycerol in PBS for 1.5–3 min. The shocked cells are washed and fed with culture medium. Until induction of MT-II-controlled expression, the medium contains F12/DMEM21 1:1 with 10% FBS. A day later, the cells are subjected to 1 mg/ml G418 to provide a pool of G418-resistant colonies. Successful transformants, also having a stable inheritance of the desired plasmid, are then plated at low density for purification of clonal isolates.

Assay for Production Levels of ASP

The transformants are assayed for production of the desired protein, first as pools, and then as isolated clones in multi-well plates. The plate assay levels are somewhat dependent on the well size—e.g. results from 24 well plates are not directly comparable with those from 96 well plates. Clones which are found by plate assay to be producing the protein at a satisfactory level can then be grown in production runs in roller bottles. Typically, the levels of production are higher when the scale up is done. However, there is not an absolute correlation between performance in the plate assay and in roller bottles—i.e. cultures which are the best producers in the plate assay are not necessarily the best after scale-up. For this reason, typically 100–200 or more individual clones are assayed by various screening methods on plates and 5–10 of the highest producers are assayed under production conditions (roller bottle).

Plate Assays

Pools of cells transformed with the various ASP encoding plasmids were grown in multi-well plates and then exposed to $5 \times 10^{-5}$ to $1 \times 10^{-4}$ zinc ion concentration to induce production of ASP. ASP assays were conducted using Western blot employing immunoprecipation with rabbit anti-human ASP polyclonal antiserum followed by $^{125}$I Protein A and autoradiography.

In more detail, semiconductor monolayers of individual cell lines growing in McCoy's 5A medium with 10% FBS were washed with phosphate-buffered saline (PBS) and refed with McCoy's containing 10% FBS, $1 \times 10^{-4}$ zinc chloride, and 0.25 mM sodium ascorbate. (Ascorbate may be helpful in mediating the hydroxylation of proline residues.) Twenty-four hours post induction, the cells were washed with PBS and refed with serum-free McCoy's containing the zinc chloride and ascorbate. After 12 hours, the conditioned media were harvested, made 20 mM in Tris, pH 8, and filtered through nitrocellulose in a BRL dot-blot apparatus. The nitrocellulose filter was blocked in 50 mM Tris, pH 7.5, 150 mM NaCl (Tris/salt) containing 5% nonfat dry milk, and then incubated with 1:5000 dilution of rabbit anti-human ASP polyclonal antiserum in the blocking solution, washed several times in the above Tris/salt, and incubated with 25 μCi of $^{125}$I protein A in blocking solution, washed, and autoradiographed.

Most pools transformed with the ASP encoding vectors did not produce ASP detectable in this assay. However, a positive, ASP-secreting cell line, designated A-38, was selected from pMT-Apo:gHS(HinfI/EcoRI) transformants. In addition, certain pools from cells transformed with pASPc-SV(10), designated ASP-I, or with pASPcg-SV(10), designated ASP-F and ASP-G, produced levels of ASP comparable to those produced by the cell line designated D-4 described below (~2-5 μg/ml).

Characterization of ASP Protein

The A-38 cells (supra) were grown to 25% confluence in McCoy's 5A medium containing 10% FBS and then induced with $10^{-4}$M zinc chloride in McCoy's containing 10% FBS and 0.25 mM sodium ascorbate. (Half of the cells were also treated with $10^{-6}M$ dexamethasone.) Twenty-four hours later, the cells were washed with PBS and refed with RPMI medium containing 10% dialyzed FBS, $1\times10^{-4}M$ zinc chloride, 0.25 mM sodium ascorbate, and 0.5 mCi/ml $^{35}$S-methionine.

Figure 10:
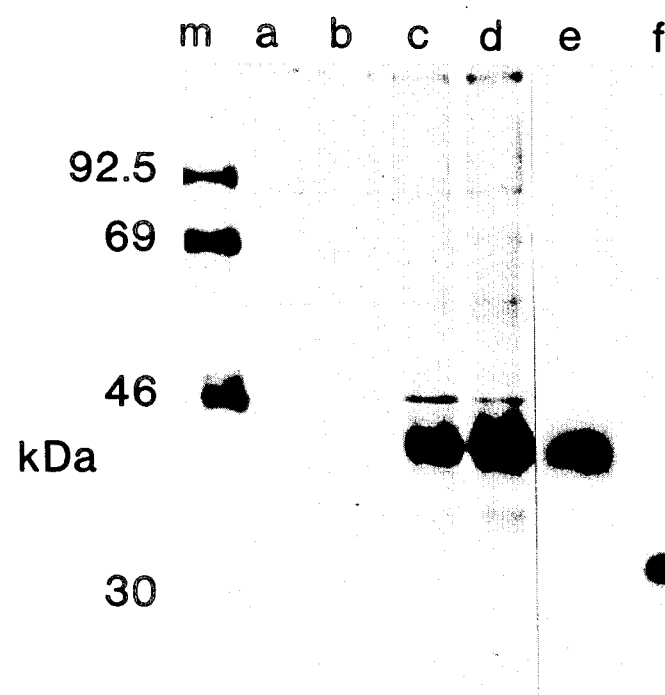
FIG. 10 shows the results of SDS PAGE conducted on $^{35}S$ labeled supernatant proteins, with and without treatment with endo F, secreted by pMT-Apo:gHS(-HinfI/EcoRI) transfected CHO cells.

Eighteen hours later, the cell supernatant was made 1 mM phenylmethylsulfonylfluoride and immunoprecipitated with rabbit anti-canine ASP antiserum using protein A as carrier. Half of the precipitated protein was boiled in SDS-PAGE sample buffer, and the other half eluted into 0.75% Triton X-100, 0.075% SDS, 0.75% 2-mercaptoethanol, 30 mM EDTA, 75 mM sodium phosphate, pH 1 and incubated for 1 hr at 37° with 0.5 units of endoglycosidase-F (endo-F). Endo-F treated and untreated protein fractions were subjected to SDS-PAGE with the results shown in FIG. 10. The Endo-F treated fraction showed a 30 kd protein (lane F) as compared to 38 kd protein for the untreated (lane E). (Lane M contains size markers, lanes A and B supernatants from untransformed CHO cells, and lanes C and D supernatants from A-38 cells untreated and treated with dexamethasone, respectively.)

Supertransfection to Prepare D-4

An additional cell line, designated D-4, was obtained by supertransfection of A-38 with a mixture of pMT-Apo:gHS(HinfI/EcoRI) (20 μg) and pSV2:GPT (1 μg). Semiconfluent monolayers of A-38 growing in F12/DMEM21 with 10% FBS were co-transfected, as described above. After 48 hours the cells were split 1:5 into F12/DMEM21 containing 10% FBS and HAT selectiondrugs. After 17 days of HAT selection, the pool of surviving resistant clones was screened for individual clones producing high levels of ASP by the immunofilter screen method of McCracken, A. A., et al *Biotechniques* (March/April 1984) 82–87. Briefly, the cells were seeded onto plates at 100 cells per 100 mm dish in F12/DMEM21, 10% FBS. After 5 days (when colonies contain 50-200 cells each), the cells were washed with PBS, refed with serum-free F12/DMEM21, and overlayed with a sterile teflon mesh. On top of the mesh was placed a nitrocellulose filter which was left in place for 8 hr. The nitrocellulose was removed and treated as an immunoblot, first with rabbit anti-canine ASP polyclonal antiserum, then $^{125}$I protein A, followed by autoradiography. Of approximately 2000 colonies screened, two gave a detectable signal and one, designated D-4, was shown to express the ASP gene at 10-20 times the level of A-38, or at an amount corresponding to an estimated 2-5 μg/ml ASP.

Characterization

The secreted ASP from the D-4 cell line was isolated from the serum-free medium by affinity chromatography and sequenced at the N-terminus on a gas-phase microsequencer. Determination of a 16 amino acid sequence showed complete homology with the N-terminal portion of the protein isolated from lung lavage; 70% of the total contained an N-terminal Glu residue; the remaining 30% was clipped so as to contain an N-terminal Val (position 2 relative to Glu). This is the same composition as the isolated lavage protein. Hydroxyprolines were present at positions 10, 13, and 16, indicating the ability of the cells to exhibit post-translational processing.

Figure 11:
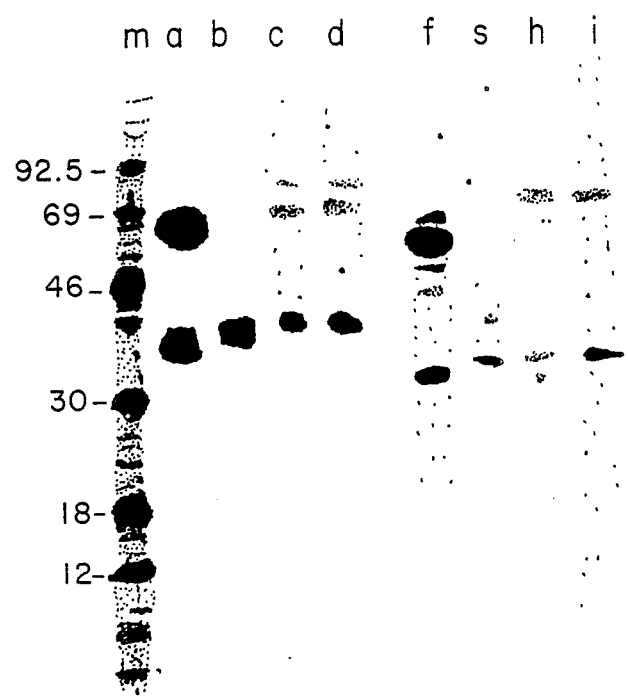
FIG. 11 shows the results of SDS PAGE immunoblotted with labeled human antiASP conducted on supernatant proteins, with and without treatment with endo F, secreted by pMT-Apo:gHS(HinfI/EcoRI) transfected CHO cells.

In addition, the protein secreted by D-4 along with the secreted protein fraction from pool ASP-I (supra) and from pool ASP-G (supra) was compared to human proteinosis lung lavage protein using Western blot. Serum-free medium from induced cells was TCA precipitated, treated (or not) with Endo-F and subjected to SDS-PAGE in 12.5% gels. The gel was electroblotted and dot-incubated with rabbit antihuman ASP polyclonal antiserum followed by $^{125}$I protein A. The results are shown in FIG. 11.

Lanes A and F contain 1 μg alveolar proteinosis protein before and after Endo-F digestion; lanes B, C, and D represent media from D-4, ASP-I pool, and ASP-G pool respectively untreated with Endo-F; lanes G, H, and I represent proteins from these supernatants treated with Endo-F. It is evident that Endo-F treatment reduces the apparent molecular weight of all proteins, and results in more discrete bands.

Production Runs

The supertransfected cell line containing multiple copies of pMT-Apo:gHS(HinfI/EcoRI) (cell line D-4) was used in a production level run in roller bottles. An 850-cm square roller bottle was seeded with a 10 cm dish containing $2\times10^6$ cells in 10% FCS, 15 mM Hepes, pen/strep, and glutamine. After the cells reached confluence (2-3 days), they were washed $2\times$ with PBS and replaced with 250 ml of F12/DMEM21, 10 mM Hepes without FCS. The following day the cells were refed with 250 ml of F12/DMEM21, 10 mM Hepes, $5\times10^{-5}$ zinc chloride, $10^{-6}M$ dexamethasone, and 0.25 mM ascorbate. The cells were harvested every 2 days, spun for ten minutes at 1000 rpm, and frozen at $-20°$ C. Production was 1-5 μg/ml/day, assayed by dot-blot Western using polyclonal anti-canine ASP antisera at 1:5000 dilution, as described above. Production drops after about 14-17 days.

D.9. Activity of the ASP Components

The ability of the isolated ASP Components to enhance the formation of lipid film at an air/aqueous interface was assessed in vitro using the method described by Hagwood, S., et al, *Biochemistry* (1985) 24: 184–190. Briefly, a preparation of phospholipid vesicles with the appropriate ratio of test proteins is added carefully in a small volume to the bottom of a teflon dish containing aqueous buffer, a magnetic stirrer, and a platinum plate suspended at the surface of the buffer and attached to a strain gauge. Changes in surface tension registered on the strain gauge are recorded as a function of time upon starting the stirrer.

10K proteins were added to the phospholipid by mixing a chloroform solution containing them with a 2:1 v/v chloroform:methanol solution of the lipid. The solvents were evaporated, and the solids hydrated in buffer to obtain vesicles. 32K proteins can be added in aqueous solution directly to a suspension of the vesicles, and association with and aggregation of the vesicles can be detected by turbidity measurements.

As reported by Hawgood, et al (supra), 32K canine ASP was capable of aggregating phospholipid vesicles and of enhancing the formation of film when included in the phospholipid vesicles, when the phospholipids were those obtained from the canine lung surfactant complex. The activity of the proteins of the invention is assessed using the same procedures for measuring aggregation and film formation enhancement as set forth in Hawgood.

Both the phospholipid preparation from canine lung prepared as described above (300 μg) and a synthetic mixture of phospholipids were used. The synthetic phospholipid contained 240 μg of commercially available DPPC and 60 μg egg PG, and is much more reluctant to form films than is the natural lipid. However, the test phospholipid was chosen so as to dramatize most effectively the activity of the proteins.

Figure 12:
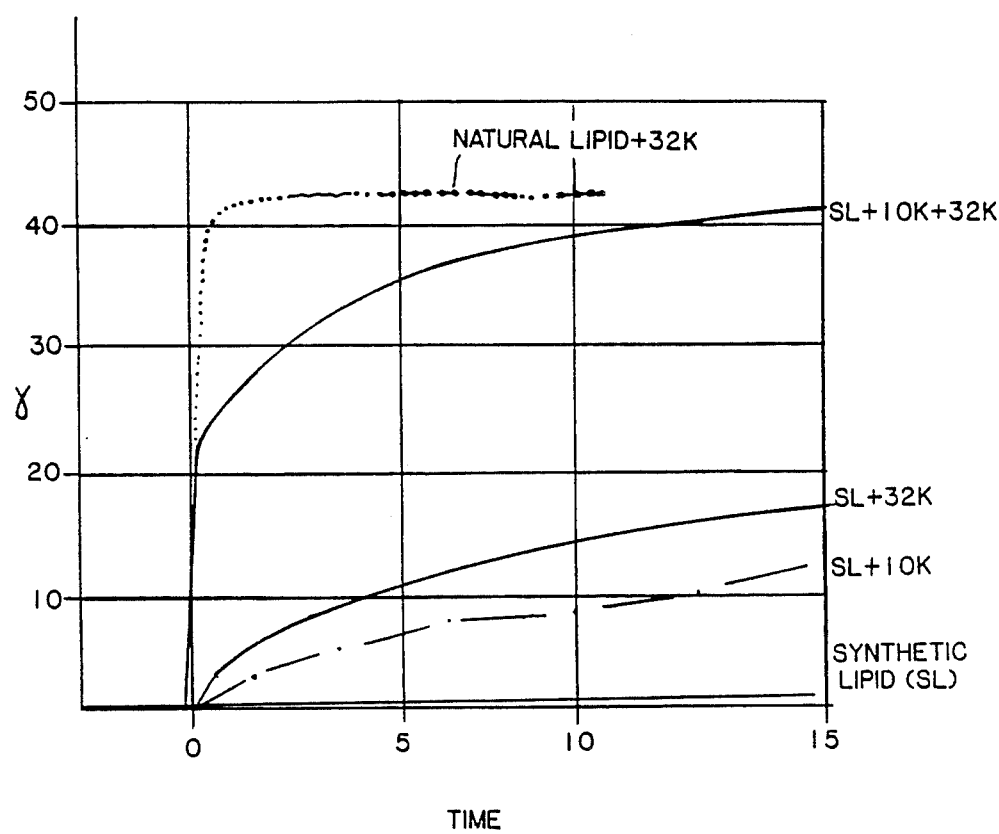
FIG. 12 shows the results of in vitro determination of the ability of ASP to enhance surface tension lowering by phospholipids.

The 32K protein and the mixture of 10K ASP were isolated from canine lung as described above. While the addition of 60 μg of the 32K protein was able to enhance film formation by the "natural" phospholipid obtained from lung almost to the level exhibited by the complex per se, it only moderately enhanced film formation using synthetic lipid. Similar results were obtained for addition of 13 μg of the 10K protein alone. However, when 13 μg of the 10K preparation was incubated with the synthetic phospholipid vesicles prior to the addition of 60 μg of 32K protein, film formation occurred at a rate and to a degree comparable to that of the natural complex per se. These results are shown in FIG. 12.

We claim:

1. A recombinant DNA sequence or a naturally occurring mutant DNA sequence thereof, which DNA sequence consists essentially of a DNA sequence which encodes mammalian 10K alveolar surfactant protein (10K ASP), which 10K ASP is encoded by a DNA which hybridizes under stringency conditions corresponding to a wash of 2×SSC, 0.1% SDS at 50° C. to human SP18 cDNA as show for nucleotides 611–1156 in FIG. 6, said DNA being free from DNA encoding additional protein normally produced in lung cells.

2. The recombinant DNA of claim 1 wherein the 10K ASP is encoded by the DNA of FIG. 2 or a naturally occurring mutant DNA sequence thereof.

3. The recombinant DNA of claim 1 wherein the 10K ASP is encoded by the DNA of FIG. 6 or a naturally occurring mutant DNA sequence thereof.

4. A recombinant expression system comprising the 10K ASP encoding DNA sequence of claim 1 which expression system is capable, when transformed into host cells, of effecting the expression of the DNA of claim 1.

5. The expression system of claim 4 which further comprises a viral enhancer.

6. The expression system of claim 5 wherein the viral enhancer is the SV40 enhancer.

7. Recombinant host cells transformed with the DNA sequence of claim 1.

8. Recombinant host cells transformed with the expression system of claim 4.

9. The cells of claim 8 which are mammalian cells.

10. The cells of claim 9 which are CHO cells.

11. A method to produce 10K ASP which comprises culturing the cells of claim 7 under conditions which effect the expression of the 10K ASP encoding DNA, and
recovering the 10K ASP produced.

12. A method to produce 10K ASP which comprises culturing the cells of claim 8 under conditions which effect the expression of the 10K ASP encoding DNA, and
recovering the 10K ASP produced.

13. A recombinant expression system of claim 4 wherein the recombinant DNA encoding 10K ASP is operably linked to control sequences compatible with mammalian host cells.

14. The expression system of claim 13 wherein said control sequences comprise the human metallothionein-2 promoter.

* * * * *